United States Patent [19]

Bouisset et al.

[11] Patent Number: 5,079,363

[45] Date of Patent: Jan. 7, 1992

[54] PROCESS FOR THE PREPARATION OF ISOQUINOLINE DERIVATIVES

[75] Inventors: Michel Bouisset; André Bousquet; Jean-Robert Dormoy; Alain Heymes, all of Sisteron, France

[73] Assignee: Sanofi, Paris, France

[21] Appl. No.: 313,545

[22] Filed: Feb. 22, 1989

[30] Foreign Application Priority Data

Feb. 23, 1988 [FR] France ............... 88 02156

[51] Int. Cl.⁵ .............. C07D 40/04; C07D 213/64; C07D 263/06
[52] U.S. Cl. .................................. 546/64; 546/70
[58] Field of Search ............... 546/62, 64, 70, 77

[56] References Cited

U.S. PATENT DOCUMENTS

| 4,013,672 | 3/1977 | Hoehn | 546/64 |
| 4,966,971 | 10/1990 | Bisagni et al. | 546/64 |

FOREIGN PATENT DOCUMENTS

| 0010029 | 9/1979 | European Pat. Off. | 546/70 |
| 2387229 | 11/1978 | France . | |
| 2422622 | 11/1979 | France . | |
| 2436786 | 4/1980 | France . | |
| 2485537 | 12/1981 | France . | |

OTHER PUBLICATIONS

Morrison and Boyd, Organic Chemistry (Boston, Allen and Bacon, 1979) pp. 992–993.
Canadian Journal of Chemistry, 59, (1981), Robins et al., pp. 2601–2607.
Journal of Organic Chemistry, 47, (1982), Meyers et al., pp. 2633–2637.
Journal of Organic Chemistry, 48, (1983), Saulnier et al., pp. 2690–2695.
Chem. Ber., 117, (1984), Vorbrüggen et al., pp. 1523–1541.
Journal of Organic Chemistry, vol. 45, 1980, pp. 4508–4511, American Chemical Society, Washington, U.S.; G. R. Newkome et al., "Pyrolysis of alkyl 2- or 6-alkoxynicotinates. An unexpected reaction".
Tetrahedron Letters, No. 47, 1978, pp. 4639–4642, Pergamon Press Ltd, Oxford, GB; G. R. Newkome et al: "Restricted N,N-dimethylnicotinamides".

Primary Examiner—Mukund J. Shah
Assistant Examiner—E. C. Ward
Attorney, Agent, or Firm—Wegner, Cantor, Mueller & Player

[57] ABSTRACT

The subject of the present invention is a process for the preparation of isoquinoline derivatives in four steps wherein use is made as synthetic intermediates of organo-lithium compounds or related compounds.

22 Claims, No Drawings

PROCESS FOR THE PREPARATION OF ISOQUINOLINE DERIVATIVES

In a general manner, the present invention relates to a novel process for the preparation of isoquinoline derivatives.

More exactly, the invnetion relates to a process for the preparation of isoquinoline derivatives of the general formula:

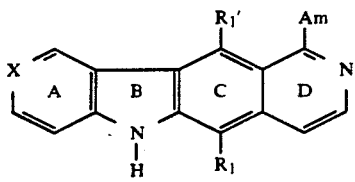

in which:
$R_1$ and $R'_1$ which are identical or different, each is selected from hydrogen and $C_{1-4}$ alkyl;
X is selected from nitrogen and $C-OR_2$ in which $R_2$ is selected from $C_{1-4}$ alkyl and benzyl,
Am represents an amino group substituted or not by a group of the formula:

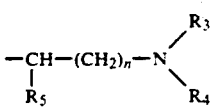

in which $R_3$ and $R_4$, identical or different, each is selected from hydrogen
and an alkyl radial having from 1 to 6 carbon atoms, $R_5$ is selected from hydrogen and an alkyl radical having from 1 to 6 carbon atoms and n represents a value of from 1 to 10.

In the present context, the expression "labile group" designates an amino protecting group which can be easily removed in basic medium such as, in particular, an arylsulfonyl group, for example benzenesulfonyl or p-toluenesulfonyl, or a monoalkyl- or di-alkylaminosulfonyl group, for example dimethylaminosulfonyl. The benzenesulfonyl, p-toluenesulfonyl or dimethylaminosulfonyl groups constitute preferred, labile groups.

The compounds of formula I are known compounds which have been published in the French patent No. 2.387.229 and its certificates of addition Nos. 2.422.622 and 2.485.537 as well as the French patent These compounds are described there as being very valuable anti-tumoral and anti-leukemic agents.

Among the compounds of formula I, more especial mention may be made of those in which $R'_1$ represents a hydrogen atom or a methyl group and $R_1$ represents a methyl group.

In addition, of the whole series of these compounds those of the general formula:

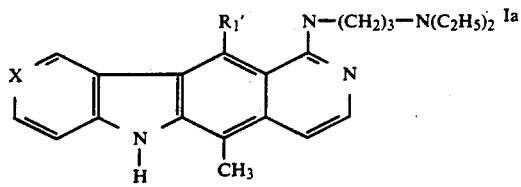

in which X represents N and $R'_1$ represents a hydrogen atom or X represents a $C-OCH_3$ group and $R'_1$ represents a methyl group, constitute preferred compounds.

The preparation of the compounds of the above-mentioned patents and certificates of addition as described therein presents numerous difficulties which makes it difficult to exploit these earlier processes on an industrial scale.

The search for a process which makes the compounds of the patents and the certificates of addition in question more readily available, in particular the compounds of formula Ia, thus remains of unquestionable importance.

In accordance with the present invention, it has been discovered that it is possible to prepare the isoquinoline derivatives of formula I in accordance with such an industrial process.

Thus, the process of the invention for the preparation of the isoquinoline derivatives in question involves the following series of steps, which will be described in a more detailed manner later:

I. First step
(a) a compound of formula

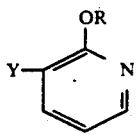

in which:
R is $C_{1-4}$ alkyl
Y is selected from 4,4-dimethyl-2-oxazolinyl and a group of the formula:

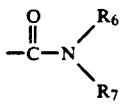

in which $R_6$ and $R_7$, which are identical or different, each represents $C_{1-4}$ alkyl, is converted into a metalated derivative of the formula:

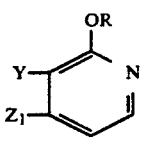

in which Z represents a lithium atom or a radical of the formula $-Mg\ Hal$, $-Mn\ Hal$ or $-Ce(Hal)_2$, Hal representing a halogen atom, then the metalated derivative of formula IVa is condensed with a heterocyclic compound of the general formula:

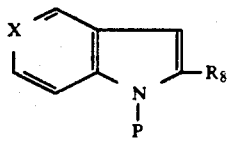

in which:
X has the same meaning as before,
P represents a labile protecting group, and
$R_8$ represents:
  a radical of formula

in which $R_1$ has the same meaning as before, or
a radical of the formula

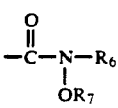

in which $R_6$ and $R_7$, which are identical or different, have the same meaning as before, or
(b) a compound of formula:

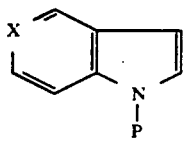

in which X and P have the same meanings as before, is converted into a metalated derivative of formula:

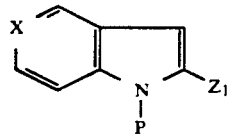

in which X, P and $Z_1$ have the same meanings as before, then the metalated derivative of formula IVb is condensed with a 2-alkoxy pyridine derivative of the general formula:

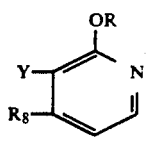

in which Y, R and $R_8$ have the same meanings as before so as to produce
in the case in which $R_8$ is a

radical, a compound of formula:

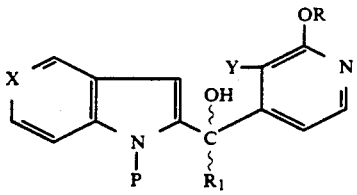

in which X, P, Y, R and $R_1$ have the same meanings as before, and
in the case in which $R_8$ is a radical of the formula

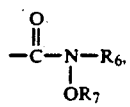

a compound of formula:

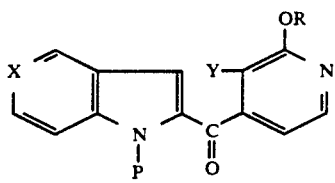

in which P, R, X and Y have the same meanings as before, a ketone which is subsequently treated by means of a reducing agent chosen from among a borohydride of an alkali metal, lithium aluminium hydride or a metal alkyl of the general formula:

$R_9M$  VII in which $R_9$ represents $C_{1-4}$ alkyl, and M represents an atom of lithium or a —Mg Hal radical in which Hal represents a halogen atom, in order to obtain a complex which is hydrolyzed to give rise to a compound of formula II and, if required, the compound of formula II, in which $R_1$ represents a hydrogen atom, is oxidized to a ketone of formula VI which is subsequently treated with a alkylmetal of formula VII and which is hydrolyzed to give rise to a compound of formula II in which $R_1$ represents $C_{1-4}$ alkyl, the compound of formula II obtained in this first step being subsequently deprotected, if required, by treatment by means of a basic agent so as to produce an N-deprotected compound.

II. Second step
The compound of formula II or the N-deprotected compound is cyclized to a lactone of formula:

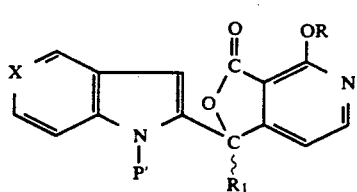

in which X, R, $R_1$ have the same meanings as before and P' designates a labile protecting group P or a hydrogen atom, then the lactone thus obtained is reduced either by means of a metal hydride to give rise to a cyclic hemiacetal of formula:

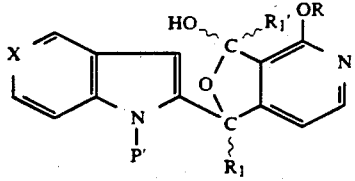

in which P', R, R₁, and X have the same meanings as before, and R'₁ represents a hydrogen atom, or by means of an alkyl magnesium halide of formula VII, with hydrolysis of the complex formed, to give rise to a hemiacetal of formula IX in which R'₁ is an alkyl radical of $C_1$-$C_4$ and, if required, deprotection is carried out. These operations of cyclization and reduction are preferably carried out by treating the compound of formula II by means of an acid in order to obtain a lactone of formula VIII, a lactone which is subjected:

to a treatment by means of a metal hydride in order to give rise to the desired cyclic hemiacetal in which R'₁ represents a hydrogen atom, to a treatment by means of an alkyl magnesium halide of formula VII, followed by hydrolysis of the complex formed in order to give rise to the desired cyclic hemiacetal in which R'₁ represents $C_{1-4}$ alkyl.

III. Third step

A compound of formula IX is converted into a compound of formula:

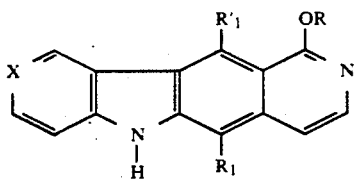

in which R, R₁, R'₁ and X have the same meanings as before.

This operation is preferably carried out by treating the hemiacetal in question with at least 10 equivalents of an alkali metal hydroxide, usually from 10 to 15 equivalents, at reflux in a $C_1$-$C_3$ alcohol, for example methanol, ethanol or isopropanol.

IV. Fourth step

A compound of formula X is treated (a) either with a compound of the general formula:

H—Am                                       XI in which Am has the same meaning as before, in the presence of an acid catalyst in order to give rise to the desired compound of formula I in the form of the free base, (b) or with dichlorophenylphosphine oxide in order to give rise to the chloro compound of the general formula:

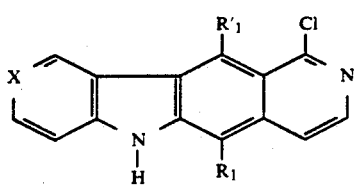

in which R₁, R'₁ and X have the same meanings as before, which is made to react with a compound of formula XI in order to form the desired compound of formula I in the form of the free base, (c) or with phosphorus trichloride in the presence of a polar co-solvent, an ammonium chloride and an aniline in order to form the chloro compound of formula XII, which is made to react with a compound of formula XI in order to give rise to the desired compound of formula I in the form of the free base, (d) or with a trimethylsilyl halide in the presence of an alkali metal halide in order to give rise to the trimethylsilyloxy derivative which is made to react with a compound of formula XI in the presence of hexamethyldisilazane and p-toluenesulfonic acid in order to form the desired compound of formula I in the form of the free base, a free base which may be treated, if necessary, with an appropriate organic or inorganic acid in order to give rise to a pharmaceutically acceptable salt.

The steps I to IV which have just been mentioned will now be described and commented on in detail:

I. First step

In order to make available a process which enables the compounds of formula I, and in particular the compounds of formula Ia, to be more readily accessible, an attempt has been made to prepare these compounds according to a novel process for building up the tetracycle ABCD which requires the creation of cycle C from, on the one hand, the entity AB bearing suitable functional or protecting groups and, on the other, the cycle D also bearing suitable functional substituents.

The compounds of the above-mentioned patents and certificates of addition, in particular the compounds of formula Ia, are characterized in particular by the presence of a dialkylaminoalkylamino chain in α to the isoquinoline nitrogen.

In order to carry out the synthesis in as straightforward a manner as possible, an attempt has been made to use N-protected pyridine compounds bearing the dialkylaminoalkylamino chain, in particular pyridine compounds of the general formula:

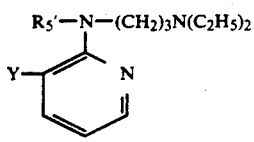

in which Y has the same meaning as before, and R'₅ represents a hydrogen atom or a protecting group, more particularly a benzyl group.

However, some of the compounds of formula XIII have proved particularly difficult to prepare and purify, in particular the compounds in which R'₅ is different from hydrogen. Such difficulties have been recorded both with regard to the reaction of a chloropyridine compound of formula:

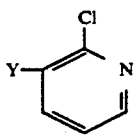

in which Y has the same meaning as before, with a secondary amine such as N-benzyl N-diethylaminopropylamine and with regard to the reaction of the compound of formula XIV with a primary amine such as benzylamine followed by possible alkylation with a diethylaminopropyl halide or vice versa.

Subsequently, attempts were undertaken to bind an atom of lithium at position 4 of the N-monosubstituted or N,N-disubstituted 2-aminopyridine derivatives thus prepared with a view to subsequently replacing this metal atom by a functional group.

For this purpose has been used either the method described in J. Org. Chem. 47, pp. 2633-2637 (1982) according to which lithiation is carried out in tetrahydrofuran at 0° C. by using lithium tetramethylpiperidide as lithiation reagent, or a similar method conducted at −78° C. and which requires, in addition, the presence of tetramethylethylenediamine as stabilization reagent of the lithium derivative.

However, the lithiation in question according to one or other of these methods and the subsequent incorporation of a functional group into compounds of formula XIII proved to be impossible in the majority of cases in particular in the case of 2-(N-3-diethylaminopropyl-N-benzyl)amino 3-diethylaminocarbonyl pyridine, 2-N-benzylamino-3-diisopropylaminocarbonyl pyridine and 2-(N-3-diethylaminopropyl)amino 3-diisopropylaminocarbonyl pyridine.

The failure of the metalation recorded at position 4 of the foregoing monosubstituted or N,N-disubstituted 2-aminopyridine derivatives may be attributed to a deactivation of this position by interfering chelation of the metalating reagent.

Even though the reaction between the chloropyridine compound of formula XIV, in which Y represents a 4,4-dimethyl 2-oxazolinyl group, and a primary amine such as benzylamine or diethylaminopropylamine or a secondary amine such as N-benzyl N-diethylaminopropylamine has proved to be much easier than in the case in which Y represents a carboxamide grouping, the lithiation in position 4 of the compounds obtained, namely 2-benzylamino 3-(4,4-dimethyl 2-oxazolinyl)-pyridine, 2-(N-3-diethylaminopropyl)amino 3-(4,4-dimethyl 2-oxazolinyl)pyridine or 2-(N-3-diethylaminopropyl-N-benzyl) 3-(4,4-dimethyl-2-oxazolinyl)pyridine has, on the contrary, not been achieved in a satisfactory manner.

Similar observations of resistance to metalation in the case of 4,4-dimethyl-2-oxazolinyl-pyridine derivatives have, moreover, been made in Tetrahedron 39, 12 pp. 1991-1999 (1983).

Similarly, it has also not been possible to bind an atom of lithium at position 4 or 2-chloro 3-diisopropylamino pyridine and 2-chloro 3-(4,4-dimethyl-2-oxazolinyl)-pyridine.

Consequently, the lithiation in position 4 of pyridine substituted at position 3 by a 4,4-dimethyl-2-oxazolinyl group or —CO NR$_6$R$_7$ group as previously described with a view to the subsequent introduction of a functional substituent appears to be particulary difficult when position 2 itself is already substituted by a secondary or tertiary amine group.

Surprisingly, it has now been found that lithiation at position 4 of pyridine bearing at position 3 a substituent such as that previously described can be carried out in a satisfactory manner starting from pyridine compounds bearing an alkoxy group at position 2, i.e. starting from compounds of formula IIIa above.

This alkoxy grouping in position 2 also offers the advantage of being able to give rise to the desired final grouping of the compounds of formula I, i.e. to the dialkylaminoalkylamino grouping after aminolysis carried out directly or after the intermediate formation of the chloro derivative.

However, when Y represents a 4,4-dimethyl 2-oxazolinyl group, R preferably represents a branched alkyl group such as isobutyl or tertiary butyl.

Thus, the first step of the process of the invention can be carried out:

A—For the preparation of a protected compound of formula II (1) by reacting a 2-alkoxy pyridine derivative of formula IIIa in a solvent with a lithiation reagent which is either a branched alkyllithium or a lithium amide at a temperature between −80° C. and −20° C. in the presence of a stabilizing reagent such as tetramethylethylenediamine or a tris(dioxa-alkyl)amine such as, for example, tris(dioxa-3,6 heptyl)amine in order to produce 4-lithio derivatives of the general formula:

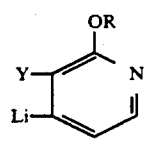

in which R and Y have the same meanings as before, (2) Then by condensing the metalated derivative of formula XV obtained in a solvent and at a temperature between −80° C. and −20° C. with a compound of formula Va in which R$_8$ represents:
a radical of the formula

as previously defined, in order to obtain N-protected compounds of formula II, or
a radical of formula

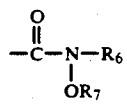

as previously defined,
in order to obtain N-protected ketones of formula VI, ketones which are subsequently treated in a suitable solvent such as an ether, for example tetrahydrofuran and at a temperature lower than or equal to ambient temperature, with a suitable reducing agent such as sodium borohydride, lithium aluminium hydride or a alkylmetal of formula VII in order to give rise to a complex that on controlled hydrolysis, for example in the presence of ammonium chloride, gives rise to the desired compounds.

Usually, the solvent used in the sequences (1) and (2) may be an ether, for example tetrahydrofuran, an ether/hydrocarbon mixture for example tetrahydrofuran/cyclohexane or pentane, an e ether/tetramethylethylenediamine mixture for example tetrahydrofuran/tetramethylethylenediamine or even tetramethylethylenediamine alone.

The alkyllithium, which is advantageously branched, is preferably tertiary butyllithium. In fact, it appears to be disadvantageous to use directly unbranched alkyllithiums on account of the possibilities of 1-2 or 1-4 addition reactions to the pyridine.

The lithium amide usually used is lithium 2,2,6,6-tetramethylpiperidide or a lithium dialkylamide such as for example lithium diethylamide or lithium diisopropylamide.

In view of its strongly basic properties, lithium 2,2,6,6-tetramethylpiperidide constitutes the preferred lithium amide according to the invention.

1 to 2 equivalents of lithiation reagent are used per equivalent of the 2-alkoxypyridine compound of formula IIIa. It has been noted that metalation is only optimal, i.e. equal to or higher than 80%, when an excess of lithiation reagent is used, for example 1.7 equivalents of lithium 2,2,6,6-tetramethylpiperidide or 1.5 equivalents of tertiary butyllithium (degree of metalation: $\geq 85\%$).

The utilization of such an excess of lithiation reagent implies that the equilibrium is displaced towards the formation of the 4-lithio derivative. This hypothesis is reinforced by the fact of a higher degree of metalation being obtained with lithium 2,2,6,6-tetramethylpiperidide than with the less basic lithium diisopropylamide when they are used at equal stoichiometry.

The main function of the tetramethylethylenediamine or the tris(dioxa-alkyl)amine is to increase the basicity of the metalating reagent and to stabilize the 4-lithio derivatives of formula XV by ligand binding.

In fact, it has been noted that the absence of a such a stabilization reagent or the utilization of temperatures higher than those envisaged in the process of the invention lead to a drop in yields. Usually, from 1 to 5 equivalents of stabilization reagent, and preferably 1-2 equivalents, are used per equivalent of compound of formula IIIa.

Thus, the metalation of the compounds of formula IIIa for the preparation of the lithium derivatives of formula XV can be carried out by employing the reagents in different ways, namely:

the extemporaneous preparation of the lithium amide by reaction of n-butyllithium with the corresponding amine, for example diethylamine, diisopropylamine or 2,2,6,6-tetramethylpiperidine and addition of this lithiated amide to a solution of the compound of formula IIIa and the stabilization reagent;

the extemporaneous preparation of the lithium amide by reaction of n-butyllithium with the corresponding amine in the presence of the stabilization reagent and addition of this solution of lithiated amide/stabilization reagent to a solution of the compound IIIa;

addition of tertiary butyllithium, for example 1.5 equivalents, to a solution of stabilization reagent and compound of formula IIIa, for example 1 equivalent of the compound of formula IIIa.

This last method offers the advantage of using a single commercial reagent, tertiary butyllithium. Consequently, the prior preparation of the lithiation reagent is avoided, in contrast to the first two procedures and this makes it possible to use a single reactor for the metalation:

slow addition of n-butyllithium to a mixture of amine, stabilization reagent and the compound of formula IIIa such as, for example, 1.5 equivalents of n-butyllithium to a mixture of 0.5 equivalents of amine, 1.5 equivalents of stabilization reagent and 1 equivalent of compound of formula III so as to form the lithium amide in situ. When the stabilization reagent is tetramethylethylenediamine (TMEDA), this gives rise to the following reaction scheme:

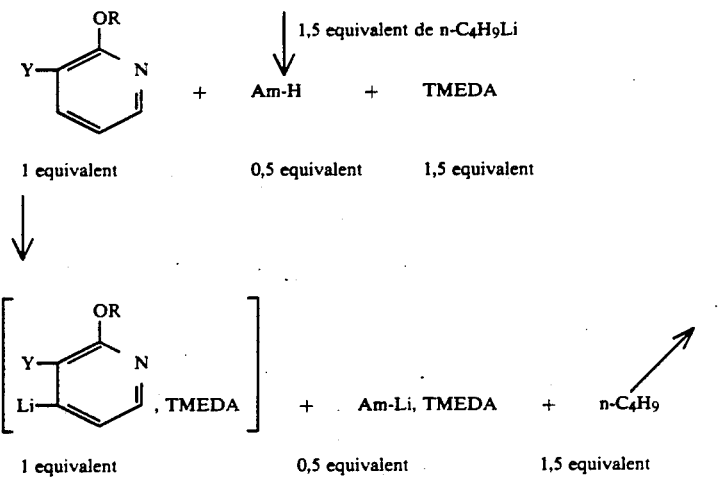

Am=diethylamino, diisopropylamino, tetramethylpiperidino.

This method offers the advantage of using only a single cooled reactor and a single reaction medium.

It also makes it possible to use only the minimum quantity of amine with respect to the amount of the derivative of formula IIIa and this is particularly advantageous when the amine in question is difficultly accessible on an industrial scale as is 2,2,6,6-tetramethylpiperidine.

In addition, this method causes the displacement of the metalation reaction towards the formation of the lithiated compound as a result of the liberation of n-butane and the absence of any free amine in the medium when the addition of n-butyllithium is complete.

The lithiated derivatives of formula XV thus produced can be isolated by removal of the solvent used at the time of their preparation, for example by evaporation under reduced pressure. For this operation, it is advisable to maintain the temperature below $-60°$ C. so as to avoid the risks of decomposition. The lithiated derivatives in question must also be stored at low temperature, otherwise they polymerize, and in an anhydrous environment in view of the ease with which they are decomposed by water.

For this reason, it will be preferable to use the lithiated derivatives of formula XV without isolation by reacting them directly in the medium in which they are produced with a compound of formula Va.

It has been possible to readily estimate the degree of metalation at position 4 of the compounds of formula IIIa, in particular 3-diisopropylaminocarbonyl 2-methoxy pyridine by using trimethylsilyl chloride as reagent with electrophilic character, since this reagent is inert towards lithium 2,2,6,6-tetramethylpiperidide at −70° C.

For this purpose the following technique has been used:

A solution of 0.1 mole of 3-diisopropylaminocarbonyl 2-methoxy pyridine, 0.17 mole of tetramethylethylenediamine and 0.35 mole of chlorotrimethylsilane in 20 ml of tetrahydrofuran is cooled to −70° C. 0.17 mole of lithium 2,2,6,6-tetramethylpiperidide, obtained by reaction of 0.17 mole of n-butyllithium and 0.17 mole of 2,2,6,6-tetramethylpiperidine in 120 ml of tetrahydrofuran, is then added to the solution within a few minutes while maintaing the temperature of the medium equal to or below −70° C. The reaction mixture is poured into an aqueous solution of hydrochloric acid (57 ml of 37% acid-150 ml of water) and extracted with toluene. After drying over sodium sulfate and evaporation of the solvent, 3-diisopropylaminocarbonyl 2-methoxy 4-trimethylsilylpyridine is obtained in the form of an oil in a yield of 79%.

NMR spectrum (CDCl$_3$): 0.3 ppm (s, 9H); 1.05-1.7 ppm (m, 12H); 3.2-3.8 ppm (m, 2H); 3.9 ppm (s, 3H); 7.0 ppm (d, 1H); 8.1 ppm (d, 1H).

This method in which the electrophilic reagent is introduced with the metalating reagent enables a good estimation of the degree of metalation to be made. The 4-lithio derivative is trapped as soon as it is formed and the decomposition reactions of this lithiated compound and possible interfering reactions are kept to a minimum.

It has also been possible to estimate the degree of metalation by reaction of 3-diisopropylaminocarbonyl 4-lithio 2-methoxypyridine with D$_2$O or CH$_3$OD (deuteration) according to the following scheme by using the method of preparation previously described:

ance of the doublet which can be attributed to the H$_4$ proton and the simplification of the H$_5$ proton which becomes a single doublet instead of a double doublet. There is no longer any H$_5$H$_6$ coupling.

Integration of the appropriate signals makes it possible to estimate with high accuracy the relative amounts of the two species and hence the degree of metalation corresponding to $$\frac{\text{Compound (C')}}{\text{Compound (A') + (C')}}$$

Yield of derivative (C'): 95%.

Degree of metalation: >86% determined by $^1$H NMR.

NMR spectrum (CDCl$_3$): 0.9-1.7 ppm (m, 12H); 3.2-3.8 ppm (2m, 2H); 3.95 ppm (s, 3H); 6.9 ppm (d, 1H); 8.15 ppm (d, 1H).

The extent of lithiation at position 4 of 3-diethylaminocarbonyl 2-methoxypyridine was also estimated by reaction of the lithiated derivative in question with D$_2$O according to the method previously described.

3-dimethylaminocarbonyl 4-deuterio 2-methoxypyridine was thus obtained in a yield of 87%.

M.p.: 82° C.

NMR spectrum (CDCl$_3$): 1.05 and 1.25 ppm (2t, 6H); 3.15 and 3.55 ppm (2s, 4H); 3.95 ppm (s, 3H); 6.9 ppm (d, 1H); 8.15 ppm (d, 1H).

Instead of the lithiated derivatives of formula XV other metalated derivatives can also be used in the procedure described above, such as derivatives of formula XV in which the lithium atom has been replaced by a —Mg Hal, —Mn Hal or —Ce(Hal)$_2$ radical, in which Hal represents a halogen atom such as chlorine, bromine or iodine.

These derivatives of magnesium, manganese or cerium can be prepared by transmetalation or exchange reaction between the 4-lithio derivatives of formula XV and a magnesium halide such as magnesium bromide, a manganese halide such as manganese chloride or a trihalide of cerium such as cerium trichloride and this, at a temperature between −70° C. and −20° C.

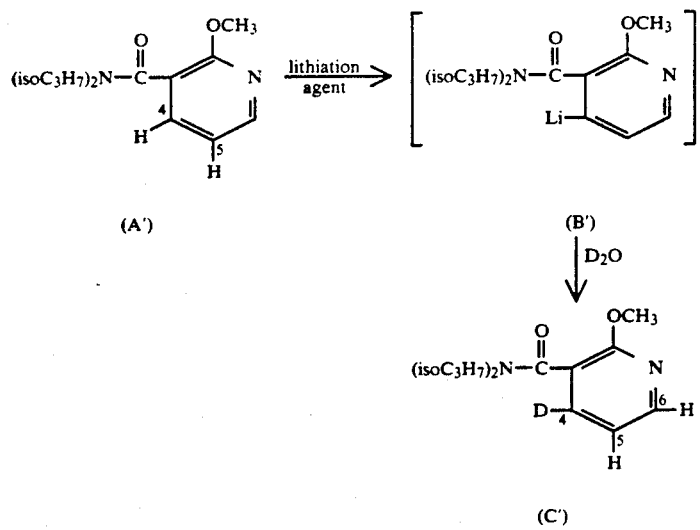

Inspection of the $^1$H NMR spectrum of the compounds obtained in the crude state shows the disappear- However, the presence of stabilizing reagent which perturbs the reaction in question must sometimes be avoided in this transmetalation reaction.

The condensation of the compounds of formula Va at position 4 of the metalated compounds of formula XV can also be carried out by different methods such as:

the simultaneous addition of lithium amide prepared extemporaneously and the compound of formula IVa to a solution of the compound of formula IIIa and the stabilization agent, simultaneous addition of lithium amide, prepared extemporaneously in the presence of the stabilization agent and the compound of formula Va to a solution of the compound of formula IIIa, metalation of the compound of IIIa as previously explained in order to form the lithiated derivative of formula XV, followed by condensation with the compound of formula Va.

This last method, according to a standard two-step procedure, is sometimes preferable, particularly if there are grounds for suspecting an interfering reaction between the lithiation reagent and the compound of formula Va.

In formula IIIa, when Y represents a 4,4-dimethyl 2-oxazolinyl radical, R preferably represents a branched alkyl grouping, for example isopropyl or tertiary butyl.

In fact, the ease of substitution of a slightly hindered group such as the methoxy group in α to an oxazoline can lead to side reactions when both lithiated carbon compounds and lithiated amides are used.

Only branched alkoxy groups make it possible to obtain in this case a high degree of metalation as well as a high yield of a derivative substituted by an electrophilic group at position 4.

For this purpose, the reaction is preferably carried out at temperatures of the order of $-70°$ C. by using for example tetramethylethylenediamine or tris(dioxa-3,6 heptyl)amine as stabilization reagent and tetramethylethylenediamine or a tetrahydrofuran/tetramethylethylenediamine or tris(dioxa-3,6 heptyl)amine as solvent.

Furthermore, when Y represents a grouping of the formula $-CONR_6R_7$ in the formula IIIa, the diethylaminocarbonyl and diisopropylaminocarbonyl groups constitute preferred groups.

The process thus described enables compounds of II to be prepared in yields which vary depending on the starting materials used. Usually, these yields vary between 20 and 40% when the labile protecting group P of the starting material of formula Va is an arylsulfonyl group, for example benzenesulfonyl.

These yields can be considerably improved to approach, in certain cases, 70% when a derivative of formula Va is used in which the labile protecting group P is a monoamino- or dialkylaminosulfonyl grouping such as dimethylaminosulfonyl.

The compounds of formula Va are either known substances which have been published in FR-A-2 574 406 or compounds which can be prepared by the procedure described in that document.

For example, the compounds of formula Va in which R represents a radical of the formula:

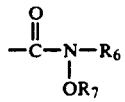

can be prepared starting from a 2-lithio derivative of N-protected 5-aza indole or a 2-lithio derivative of N-protected 5-alkoxy indole and a halide of the formula:

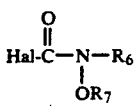

in which Hal, $R_6$ and $R_7$ have the same meanings as before.

Similarly, the starting materials for the preparation of compounds of formula Va, i.e. compounds which can be represented by the formula Va in which $R_8$ is hydrogen, can be prepared starting from 5-aza indole or a 5-alkoxy indole by first causing it to react with an alkali metal hydroxide in the presence of a phase transfer catalyst, then with a halide of formula P—Hal in which P has the same meaning as before and Hal represents a halogen atom.

According to the variant (b) of the process, compounds of formula II can also be prepared:

(1') by making a N-protected heterocyclic derivative of formula IIIb react in a solvent with a lithiation reagent which is either a branched alkllithium or a lithium amide at a temperature between $-80°$ C. and $-20°$ C. in the presence of a stabilizing reagent in order to give rise to 2-lithio derivatives of the general formula:

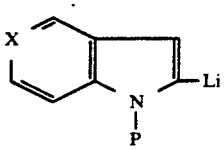

XVI in which X and P have the same meanings as before:

(2') then by condensing the metalated derivative of formula XVI obtained in a solvent at a temperature between $-80°$ C. and $-20°$ C. with a pyridine derivative of formula IVb in which $R_8$ represents:

a radical of the formula

as previously defined in order to obtain the N-protected compounds of formula II, a radical of formula:

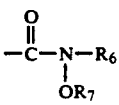

as previously defined, in order to obtain N-protected ketones of formula VII which are subsequently treated as previously described.

B—In order to carry out the deprotection of the compound of formula II, this compound is treated in a solvent by means of a basic reagent such as an alkali metal carbonate, for example potassium carbonate.

C—In order to prepared a protected compound of formula II in which R represents an alkyl group, a compound of formula II in which $R_1$ is hydrogen, i.e. a compound of formula:

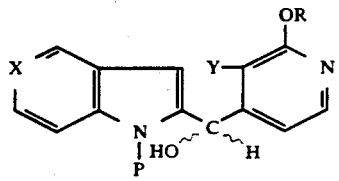   XVII in which P, X, R and Y have the same meanings as before is treated at reflux in a solvent such as dichloromethane by means of an oxidizing agent such as manganese dioxide in order to give rise to a ketone of formula VI, a ketone which is treated with a alkylmetal of formula VII, then subjected to limited hydrolysis, for example in the presence of ammonium chloride, in order to give rise to the desired compound.

The pyridine derivatives of formulae II, IIIa, IVa, Vb, VI and XVII are new compounds and they themselves constitute particularly valuable intermediates for the preparation in particular of alkoxy-isoquinoline derivatives of formula I.

Consequently, another subject of the invention relates to derivatives of 2-alkoxy pyridine of the general formula:

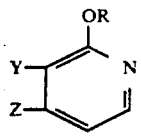   XVIII in which R and Y have the same meanings as before and Z represents:
- a hydrogen atom,
- a lithium atom or a —Mg Hal, —Mn Hal or —Ce(-Hal)$_2$ group in which Hal represents a halogen atom,
- a group of the formula:

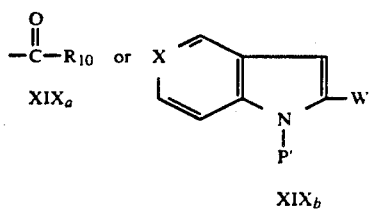

XIX$_a$     XIX$_b$ in which:
$R_{10}$ represents a hydrogen atom, $C_{1-4}$ alkyl, a hydroxyl group or a group of the formula:

in which $R_6$ and $R_7$ have the same meanings as before,

X has the same meaning as before,
P' represents a labile protecting group P or a hydrogen atom,
W represents a group of the formula:

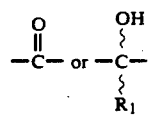

in which $R_1$ has the same meaning as before.

The invention also relates to the two isomers of the compounds of formula XVIII in which W represents a grouping:

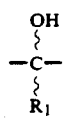

as well as to mixtures of these isomers

The compounds of formula XVIII in which Z represents a hydrogen atom or a grouping of formula XIXa can be prepared as follows:

(1) When Z represents hydrogen, by refluxing a 2-chloropyridine derivative of the general formula:

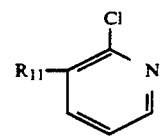   XX in which $R_{11}$ represents a —CONR$_6$R$_7$ grouping as previously defined, the radical

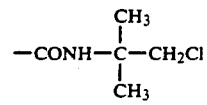

or the 4,4-dimethyl 2-oxazolinyl radical in an alcohol having from 1 to 4 carbon atoms, for example methanol, in the presence of an excess of the corresponding alkali metal alcoholate such as sodium methylate to give rise to the desired compound of formula XVIII in which Z represents hydrogen.

Consequently, the compounds of formula XVIII in which Y represents the 4,4-dimethyl 2-oxazolinyl radical can be obtained by two routes:
- a direct route, consisting of carrying out in an alcoholic/alkali metal alcoholate medium the cyclization of the radical:

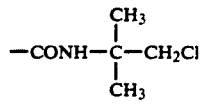

linked to position 3 and of simultaneously replacing the chlorine atom at position 2 by an alkoxy group, preferably a branched alkoxy group,
or an indirect route, consisting of treating at reflux and if necessary in a suitable solvent such as an aromatic hydrocarbon, for example toluene, the compound of formula XX above in which $R_{11}$ represents the radical:

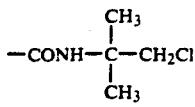

with a non-nucleophilic base such as an alkali metal carbonate or hexamethyldisilazane in order to give rise to 2-chloro 3-(4,4-dimethyl 2-oxazolinyl)pyridine, the reaction of which with an alcohol/alkali metal alcoholate mixture provides the desired derivative, preferably the derivative in which the 2-alkoxy grouping is a branched alkoxy grouping.

The pyridine derivatives of formula XX themselves can be prepared:

when $R_{11}$ represents a —CONR$_6$R$_7$ grouping as previously described, by reaction at reflux between 2-chloro nicotinic acid and thionyl chloride to form the chloride of this acid which is then made to react in an appropriate solvent, for example dichloromethane, with an amine of the general formula:

     XXI in which $R_6$ and $R_7$ have the same meanings as before, at a temperature lower than 30° C. to give rise to the desired compound, when $R_{11}$ represents the grouping:

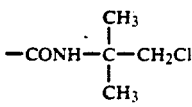

by condensing the chloride of 2-chloro nicotinic acid with 2-amino 2-methyl propanol at a temperature lower than or equal to 0° C. in a suitable solvent, for example a dichloromethane/tetrahydrofuran mixture, to form 2-chloro 3-(1,1-dimethyl 2-hydroxyethyl)amino-carbonyl pyridine which is then made to react with thionyl chloride at a temperature lower than ambient temperature to give the desired compound.

(2) When Z represents a grouping of formula XIXa, by using a similar procedure to that described previously for the preparation of the compounds of formula II starting from compounds of formulae XV and Va. However, in the present case, the compound to be condensed will be selected from the group formed by:

an ester of the general formula:

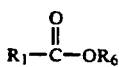

in which $R_1$ and $R_6$ have the same meanings as before,
an anhydride of the general formula:

in which $R_1$ has the same meaning as before,
an amide of the general formula:

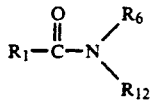

in which $R_1$ and $R_6$ have the same meanings as before and $R_{12}$ represents an $C_{1-4}$ alkyl or $C_{1-4}$ alkoxy,
a halide of the general formula:

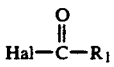

in which Hal represents a halogen atom $R_1$ has the same meaning as before,
a nitrile of the general formula:

in which $R_1$ has the same meaning as before, carbon dioxide,
a halide of the general formula:

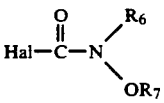

in which $R_6$ and $R_7$ have the same meanings as before and Hal represents a halogen atom, for example chlorine, to give rise to the desired compound of formula XVIII in which Z represents a grouping of the formula XIXa.

The operating conditions used in the sequences (1) and (2) of the above process, namely solvents, stabilization reagents as well as the different procedures used are identical with those described in the process of the invention requiring the utilization of the compounds of formulae IIIa, XV and Va already mentioned.

In accordance with an alternative procedure, the compounds of formula XVIII in which Z represents a grouping of formula:

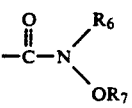

can be obtained by reacting a pyridine carboxylic acid derivative of the general formula:

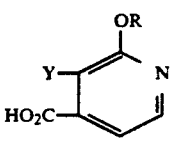     XXII in which R and Y have the same meanings as before, at ambient temperature with a hydroxylamine derivative of the general formula:

in which $R_6$ and $R_7$ have the same meanings as before, in the presence of an amide-forming reagent such as benzotriazolyl tris-dimethylaminophosphonium in order to give rise to the desired compound of formula XVIII.

When the derivative of formula XXIII is in the form of salt, for example the hydrochloride, it is preferable to carry out the reaction in the presence of an acid acceptor, for example triethylamine.

According to the invention, the compounds of formula II exhibit in particular the following advantages:
- the substituent OR can be converted into an Am grouping present in the compounds of formula I,
- the substituent Y coupled with the substituent OR makes it possible to bind an atom of lithium at position 4,
- the substituent Y is either a carboxamide sufficiently hindered at its carbonyl grouping to prevent the condensation of the lithium adduct at position 4 on itself under the conditions of metalation, or a 4,4-dimethyl 2-oxazolinyl grouping which is stable under such basic conditions,
- the substituent Y can be reduced from the oxidation state 3 to substituents of oxidation state 2 which alone are capable of leading to the closure of the ring by passing from compound VIII to the compounds X above.

II. Second step

It has been found that it is possible, starting from derivatives of formula II, to obtain a compound of formula X in the third step via the intermediary of a lactone of formula VIII, then of a cyclic hemiacetal derivative of formula IX.

These cyclic hemiacetal derivatives of formula IX can be prepared from the lactones in question in particularly high yields of the order of 85 to 95%, depending on the case.

The compound of formula IX can be obtained by first preparing a lactone of formula VIII by heating to reflux an alcohol of formula II in a suitable solvent such as ethanol in the presence of an acid such as acetic acid.

The lactone of formula VIII is then subjected to reduction:
- by means of a metal hydride, preferably diisobutylaluminium hydride, in a solvent such as dichloromethane or lithium aluminium hydride in a solvent such as, for example, tetrahydrofuran, the reaction being carried out at a temperature between −20° C. and −70° C., in order to give rise to a cyclic hemiacetal of formula IX in which $R'_1$ represents hydrogen.

Usually, 1.5 to 2 equivalents of metal hydride are used per equivalent of lactone of formula VIII,
- by means of an alkyl magnesium halide of formula VII in which M represents a —Mg Hal radical in a solvent, for example an ether such as tetrahydrofuran, at a temperature varying between −80° C. and ambient temperature and the complex formed is hydrolyzed in the presence of acetic acid for example to give rise to a cyclic hemiacetal of formula IX in which R' represents $C_{1-4}$ alkyl.

As metal hydride, it is preferable to use diisobutylaluminium hydride which confers a high selectivity on the reduction, thus avoiding the formation of appreciable amounts of products formed with more powerful reducing agents as is partially the case with lithium aluminium hydride.

The process thus described makes it possible to prepare cyclic hemiacetals of formula IX in high yields. In fact, depending on the case, it has been possible to record overall yields of from 75 to 90% starting from the compound of formula II.

In another approach, the derivatives of 6-aza 7-alkoxy phthalide of formula IX, in which P' represents a hydrogen atom, can be prepared:

(a) by treating by means of boron trifluoride etherate in an alcohol of the general formula:

$$R_{13}OH \qquad \text{XXIV}$$

in which $R_{13}$ represents $C_{1-4}$ alkyl, for example in methanol, a N-protected derivative of formula IX, namely a phthalide derivative of formula IX, in which P' represents a labile grouping in order to form a ketal of the general formula:

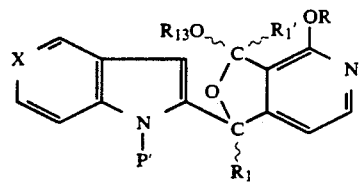

XXV in which P, R, $R_1$, $R'_1$, $R_{13}$ and X have the same meanings as before, (b) by reacting the ketal of formula XXV in a solvent, for example an aqueous solvent such as aqueous methanol, with a basic reagent such as the carbonate or bicarbonate of an alkali metal, for example potassium carbonate or bicarbonate, in order to give rise to a deprotected compound of the general formula:

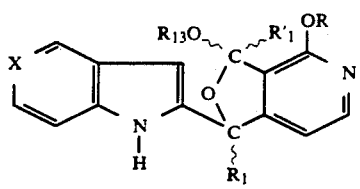

XXVI in which R, $R_1$, $R'_1$, $R_{13}$ and X have the same meanings as before, (c) by hydrolyzing the deprotected compound of formula XXVI in the presence of an acidic reagent such as hydrochloric acid or boron trifluoride etherate in order to give rise to the desired phthalide derivative of formula IX.

III. Third step

The following procedures for the reactions of the third step have been found to be particulary attractive.

Thus, as examples, it is possible to treat an equivalent of a compound of formula IX:

(a) in which X represents a nitrogen atom, P' represents a radical P and $R'_1$ represents a hydrogen atom, with 10 to 15 equivalents of an alkali metal hydroxide, preferably potassium hydroxide, for 15 to 20 hours in methanol at reflux or for 1 to 2 hours in ethanol at reflux in order to form the alkoxy-isoquinoline derivatives of formula X in which X represents a nitrogen atom, R represents $C_{1-4}$ alkyl and $R'_1$ represents a hydrogen atom, (b) in which X represents a C—$OR_2$ group, P' has the meaning indicated and $R'_1$ represents $C_{1-4}$ alkyl, with 10 to 15 equivalents of an alkali metal hydroxide, preferably potassium hydroxide, for 12 to 15 hours in methanol at reflux in order to form the alkoxy-isoquinoline derivatives of formula X in which X represents a C—$OR_2$ group and R and $R'_1$ each represents $C_{1-4}$ alkyl;

(c) in which X represents a C—$OR_2$ group, P' represents a grouping P and $R'_1$ represents a hydrogen atom, with 10 to 15 equivalents of an alkali metal hydroxide, preferably potassium hydroxide, for 1 to 2 hours in methanol at reflux in order to form the alkoxy-isoquinoline derivatives of formula X in which X represents a C—$OR_2$ group, $R'_1$ represents a hydrogen atom and R and $R_1$ have the meanings indicated.

The synthesis of compounds of formula X according to this process is the result of three chemical steps being carried out in the same reaction medium: deprotection of nitrogen, cyclization and reductive aromatization in the presence of one and the same reagent, an alkali metal hydroxide in alcoholic medium.

When milder reaction conditions are used than those recommended above, the cyclization/aromatization does not occur.

In fact, it has been observed that by reacting a phthalide derivative of formula IX in which X represents a nitrogen atom, with an alkali metal hydroxide, for example sodium hydroxide, in an alcohol having from 1 to 3 carbon atoms, for example methanol, ethanol or isopropanol, at a temperature varying between $-5°$ C. and ambient temperature, it is not the expected compound of formula X which is formed but an isoquinoline derivative of the general formula:

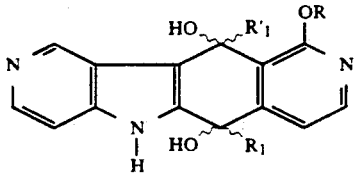

XXVII in which R, $R_1$ and R' have the same meanings as before.

Usually this last reaction is carried out in the presence of from 1 to 5 equivalents of an alkali metal hydroxide for several hours, depending on the case.

For example, it is possible to react an equivalent of a phthalide derivative of formula IX in which X represents a nitrogen atom, $R'_1$ represents a hydrogen atom and P' represents a hydrogen atom, with an equivalent of sodium hydroxide for 3 to 4 h or an equivalent of a phthalide derivative of formula IX in which X represents a nitrogen atom, $R_1$ represents $C_{1-4}$ alkyl, and P' represents a grouping P, with 4 to 5 equivalents of sodium hydroxide for 2 to 8 hours to give rise to a compound of formula XXVII.

Similarly, it has been observed that by treating a phthalide derivative of formula IX in which X represents a C—$OR_2$ group and $R'_1$ represents an alkyl radical of $C_1$-$C_4$ with an alkali metal hydroxide, preferably potassium hydroxide, in an $C_{1-3}$ alcohol, for example methanol, ethanol or isopropanol, at a temperature varying from 40° to 50° C., an alkenyl derivative of the general formula:

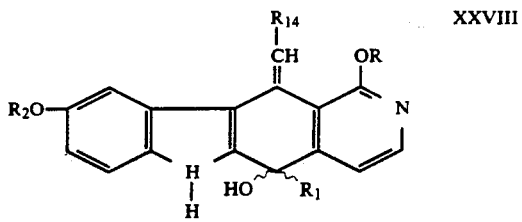

XXVIII is formed, in which R, $R_1$ and $R_2$ have the same meanings as before and $R_{14}$ represents a hydrogen atom or $C_{1-3}$ alkyl.

The reaction usually takes place in the presence of 10 to 15 equivalents of an alkali metal hydroxide during several hours, depending on the case.

For example, it is possible to react an equivalent of a phthalide derivative of formula IX in which X represents a C—$OR_2$ grouping, $R'_{14}$ represents $C_{1-4}$ alkyl, and P represents a hydrogen atom, with 10 to 15 equivalents of potassium hydroxide for 3 to 4 hours in order to obtain a compound of formula XXVIII.

On the other hand, the utilization of still milder conditions, i.e. from 1 to 5 equivalents of sodium hydroxide at a temperature of from $-5°$ C. to ambient temperature, made it impossible to bring about the cyclization of the phthalide derivatives of formula IX in which X represents a C—$OR_2$ grouping.

The isoquinoline derivatives of formula XXVII and the alkenyl derivatives of formula XXVIII can be subsequently treated for example in a glycol ether, preferably the dimethyl ether of diethylene glycol, at a temperature varying between 100° C. and reflux temperature, for example between 120° C. and 140° C., with an alkali metal borohydride such as sodium borohydride to give rise to the desired compounds of formula X.

A similar reaction to that described above starting from the compounds of formulae XXVII and XXVIII appears in J. Org. Chem. 48, pp. 2690–2695 (1983) in which an equivalent of 5,11-dihydroxy 5,11-dimethyl 10,11-dihydro 5H-pyrido[3,4-b]carbazole is made to react with about 40 equivalents of sodium borohydride for 20 hours in refluxing ethanol to give rise to 5,11 dimethyl 10H-pyrido[3,4-b]carbazole.

The need to use a very large excess of sodium borohydride in this process is owing to the concurrent destruction of the latter by reaction with the refluxing ethanol.

However, the use of such an excess makes it difficult to work up the reaction mixture at the end of the reaction owing to the large amounts of boron salts. For this reason, the compounds obtained must be purified by chromatography. Now it has been found, within the framework of the invention, that the replacement of ethanol by a glycol ether, for example the dimethyl ether of diethyleneglycol, makes it possible to reduce considerably the excess of sodium borohydride required from 40 equivalents to 2 to 3 equivalents, for example, and conduct the reaction at a higher temperature for a very short time, for example at a 120°–140° C. for 0.5 hour. This procedure makes it possible to obtain the compounds of formula X in yields of over 90%.

IV. Fourth step

In the French patents previously cited a process is described which makes possible in particular the preparation of derivatives of formula I above from pyridones of the general formula:

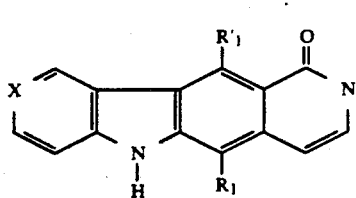

in which X, $R_1$ and $R'_1$ have the same meanings as in formula I, by treatment at reflux with an excess of phosphorous trichloride to give the chloro derivative of formula XII and amination of the chloro derivative in question at reflux.

One of the major problems encountered in this type of synthesis lies in the low solubility of the compounds of formula XXIX in organic solvents. However, the utilization of a very large excess of phosphorous trichloride as reagent and solvent can be envisaged for the preparation of the compounds of formula XII. In spite of the improved solubility thus obtained, the chlorination is, however, difficult to achieve on account of the heterogeneity of the medium, which leads to the need for a special type of stirring on an industrial scale, for example by use of a fluidized bed.

In contrast, the compounds of formula I can be obtained easily in high yield starting from an alkoxy-isoquinoline of formula X, for example from a compound with a methoxy group.

The alkoxy derivatives in question possess a considerably higher degree of solubility in the usual solvents, in particular acetonitrile, than the pyridones of formula XXIX. Consequently, these alkoxy derivatives of formula X readily provide access to the chloro derivatives of formula XII without necessitating the use of such a large excess of phosphorous trichloride as in the previous procedure.

Furthermore, the alkoxy derivatives of formula X can give rise to the chloro derivatives of formula XII, without passing by the intermediary of the pyridones of formula XXIX, which avoids the step involving the conversion of the compounds of formula XXIX to the compounds of formula XII.

Moreover, the alkoxy compounds of formula X can give rise to the compounds of formula I, for example to the compounds of formula Ia, by direct replacement of the alkoxy group by an amine, for example diethylaminopropylamine, in which they are soluble.

This represents a considerable advantage since this procedure avoids the intermediate preparation of both the pyridones of formula XXIX and the chloro derivatives of formula XII.

As a consequence, the compounds of formula I are obtained by using a process according to which:

(a) either a compound of formula X is treated at reflux with a compound of formula XI in the presence of an acid catalyst, for example 2 to 4 equivalents of hydrogen chloride or trifluoromethanesulfonic acid in order to give rise to the aminated derivatives of isoquinoline of formula I in the form of the free base.

On account of the simplicity of the procedure, this method is superior to the other three variants (b), (c) and (d) which are set out below;

(b) or, a compound of formula X is treated at reflux with dichlorophenylphosphine oxide in order to give rise to the chloro compound of formula XII which is then reacted at reflux with a compound of formula XI in order to give rise to the desired compound of formula I in the form of the free base.

(c) or, a compound of formula X is treated at reflux according to the method described in Can. J. Chem. 59, 2601 (1981) with phosphorous trichloride in the presence of a polar co-solvent, for example acetonitrile, an ammonium chloride, for example triethylbenzylammonium chloride, and an aniline such as diethylaniline, in order to form the chloro compound of formula XII which is made to react at reflux with a compound of formula XI in order to give rise to the desired compound of formula I in the form of the free base.

The utilization of a polar co-solvent makes it possible to increase the homogeneity of the reaction medium, the function of the ammonium chloride is to increase the chloride ion concentration of the medium and thus accelerate the reaction, whereas the aniline derivative has the effect of partially dissolving the compound of formula X while at the same time trapping the alkyl chloride formed as an intermediate and thus preventing the alkylation of the compound of formula X in question. In the absence of the aniline derivative, a N-alkylpyridone derivative of similar structure to the compounds of formula XXIX can be isolated as sideproduct:

(d) or, a compound of formula X is treated according to the method described in Chem. Ber. 117, 1523–1541 (1984), by means of a trimethylsilyl halide, for example the chloride, in the presence of an alkali metal halide, preferably the iodide, in order to obtain a trimethylsilyloxy derivative which is made to react at reflux with a compound of formula XI in the presence of hexamethyldisilazane and p-toluenesulfonic acid as catalyst in order to form the desired compound of formula I in the form of the free base. The following, non-limiting examples illustrate the invention:

EXAMPLE 1

Preparation of 3-diethylaminocarbonyl 2-methoxy pyridine (a) 2-chloro 3-diethylaminocarbonyl pyridine 35.5 g (0.2 mole) of 2-chloro nicotinic acid and 120 ml (8.3 equivalents) of thionyl chloride are introduced into a round-bottomed flask and maintained at reflux for 3 hours. The excess thionyl chloride is distilled at atmospheric pressure and the residues of thionyl chloride are removed by azeotropic distillation in the presence of toluene.

The brownish residue of 2-chloro nicotinic acid chloride crystallizes on cooling and is used as such in the next step.

The acid chloride obtained in the preceding reaction is dissolved in 100 ml of dry dichloromethane and the reaction vessel is cooled to below 10° C. 62 ml (0.6 mole) of diethylamine dissolved in 20 ml of dichloromethane are then added during 1 h to 1.5 h while the temperature is maintained below 30° C. The organic phase is washed twice with 20 ml of water, dried over sodium sulfate, decolorized with active charcoal and then filtered.

After evaporation of the solvent, 41 g of a brown oil are obtained which after purification by distillation give 36.2 g of 2-chloro 3-diethylaminocarbonyl pyridine.

Yield: 85%.

B.p.: 116° C. (0.1 mm Hg).

| Elemental analysis %: | | | |
|---|---|---|---|
| | C | H | N | Cl |
| Calculated | 56.47 | 6.16 | 13.17 | 16.67 |
| Found | 55.21 | 6.11 | 13.83 | 16.20 |

| I.R. spectrum (film): | |
|---|---|
| aromatic C—H | 3050 cm$^{-1}$ (w) |
| C=O | 1630 cm$^{-1}$ (S) |
| aromatic C—C | 1575 cm$^{-1}$ (S) |

NMR spectrum (CDCl$_3$): 1–1.5 ppm (2t,6H); 3–4 ppm (2Q,4H); 7–8.5 ppm (m,3H).

By means of the same procedure, except that diisopropylamine is used instead of diethylamine, 2-chloro 3-diisopropylaminocarbonyl pyrine is obtained.

Yield: 99%.
M.p.: 117° C.

| Elemental analysis %: | | | |
|---|---|---|---|
| | C | H | N | Cl |
| Calculated | 59.87 | 7.12 | 11.64 | 14.75 |
| Found | 59.68 | 7.26 | 11.30 | 15.19 |

| I.R. spectrum (KBr): | |
|---|---|
| aromatic C—H | 3060 cm$^{-1}$ (s) |
| C=O | 1630 cm$^{-1}$ (S) |
| aromatic C—C | 1570 cm$^{-1}$ (S) |

NMR spectrum (CDCL$_3$): 1.1; 1.2 and 1.3 ppm (3d,12H); 3–4 ppm (m,2H); 7.1–7.7 ppm (m,2H); 8.4 ppm (m, 1H)

(b) 3-Diethylaminocarbonyl 2-methoxy pyridine

A solution of sodium methylate is prepared by the gradual addition of 22 g (0.96 mole) of pieces of sodium to 280 ml of methanol which is refluxed until the solid has completely disappeared. 40.9 g (0.192 mole) of 2-chloro 3-diethylaminocarbonyl pyridine dissolved in a 160 ml of absolute methanol are then added rapidly and the solution is refluxed for 12 hours.

The excess of sodium methylate is neutralized with a solution of 3M hydrogen chloride in methanol and the sodium chloride formed is filtered off. The methanol is removed under reduced pressure and the residue is taken up in dichloromethane. After removal of residual sodium chloride by filtration, the solvent is evaporated to give 38.9 g of 3-diethylaminocarbonyl 2-methoxy pyridine in the form of yellowish white crystals.

Yield: 97%.
M.p.: 83° C.

| Elemental analysis %: | | |
|---|---|---|
| | C | H | N |
| Calculated | 63.44 | 7.74 | 13.45 |
| Found | 63.63 | 7.89 | 13.44 |

| I.R. spectrum (KBr): | |
|---|---|
| C=O | 1625 cm$^{-1}$ |
| C—N | |

| I.R. spectrum (KBr): | |
|---|---|
| aromatic C—C | 1580 cm$^{-1}$ |

NMR spectrum (CDCl$_3$): 1.0–1.5 ppm (2t,6H); 3.25 and 3.65 ppm (2q,4H); 4.0 ppm (s,3H); 6.8–8.3 ppm (m,3H).

In a similar manner but by refluxing 2-chloro 3-diisopropylaminocarbonyl pyridine and sodium methylate for 45 hours, 3-diisopropylaminocarbonyl 2-methoxy pyridine is obtained.

Yield: 98%.
M.p.: 109° C.

| Elemental analysis %: | | |
|---|---|---|
| | C | H | N |
| Calculated | 66.07 | 8.53 | 11.86 |
| Found | 66.55 | 8.85 | 11.56 |

| I.R. spectrum (KBr): | |
|---|---|
| aromatic C—H | 3100-3000 cm$^{-1}$ (s) |
| C=O | 1620 cm$^{-1}$ (S) |
| aromatic C—C | 1580 cm$^{-1}$ (m) |

NMR spectrum (CDCl$_3$): 1.15 and 1.55 ppm (t and d,12H); 3.5 ppm (m,2H); 4.0 ppm (s,3H); 6.9–8.15 ppm (m,3H).

EXAMPLE 2

Preparation of 2-tert.butoxy 3-(4,4-dimethyl 2-oxazolinyl)pyridine (a) 2-chloro 3-(1,1-dimethyl-2-hydroxy-ethyl)aminocarbonyl pyridine 134 ml (1.4 mole) of 2-amino 2-methyl propanol are dissolved in 600 ml of a dichloroethane/tetrahydrofuran mixture (85/15 v/v) and the solution is cooled in an ice/sodium chloride bath. 70.4 g (0.4 mole) of 2-chloro nicotinic acid chloride, prepared as described in Example 1 and dissolved in 770 ml of a dichloromethane/tetrahydrofuran mixture (85/15 v/v) are added such that the temperature is maintained at or below 0° C.

When the addition is complete, stirring is continued for 0.5 h at 0° C., then at ambient temperature for 1 h. The precipitated amine hydrochloride is filtered off and the solvents are evaporated under reduced pressure. The resulting oil is dissolved in 2.5 l of chloroform and the solution is washed with 12N hydrochloric acid until the pH=5–6 in order to remove the excess amino alcohol. After decoloration with active charcoal, drying over sodium sulfate and evaporation of the solvent, 88.9 g of 2-chloro 3-(1,1-dimethyl-2-hydroxy-ethyl)aminocarbonyl pyridine are obtained in the form of an off-white powder.

Yield: 97%.
M.p.: 104° C.

| Elemental analysis %: | | | |
|---|---|---|---|
| | C | H | N | Cl |
| Calculated | 52.52 | 5.73 | 12.25 | 15.50 |
| Found | 52.27 | 6.02 | 12.17 | 15.18 |

| I.R. spectrum (KBr): | |
|---|---|
| NH, OH | 3250 cm$^{-1}$ (m,w) |
| C=O | 1670 cm$^{-1}$ (S) |
| aromatic C—C | 1570 cm$^{-1}$ (m) |

NMR spectrum (CDCl$_3$): 1.4 ppm (s,6H); 3.6 ppm (s,2H); 3.9 ppm (s,1H); 6.6 ppm (s,1H); 7–8.5 ppm (m,3H).

(b) 2-chloro 3-(1,1-dimethyl 2-chloro-ethyl)aminocarbonyl pyridine 76.8 g (0.336 mole) of 2-chloro 3-(1,1-dimethyl-2-hydroxy-ethyl)aminocarbonyl pyridine are placed in a reaction vessel immersed in a cooling bath (ice + water). 244 ml (3.36 moles) of thionyl chloride are then added so as to maintain the temperature below 20° C.

Stirring is continued for 2.5 h at 20° C. and the thionyl chloride is evaporated under reduced pressure (temperature <50° C.). After removal of the residual thionyl chloride by azeotropic distillation with toluene, 75 g of 2-chloro 3-(1,1-dimethyl 2, -chloro ethyl)amino carbonyl pyridine are obtained in the form of a pale yellow powder.

Yield: 91.5%.
M.p.: 120° C.

| | Elemental analysis %: | | | |
|---|---|---|---|---|
| | C | H | N | Cl |
| Calculated | 48.60 | 4.89 | 11.34 | 28.69 |
| Found | 48.42 | 4.97 | 11.37 | 27.72 |

| I.R. spectrum (KBr): | |
|---|---|
| NH | 3350 cm$^{-1}$ (m) |
| aromatic C—H | 3070 cm$^{-1}$ (m) |
| C=O | 1635 cm$^{-1}$ (S) |

NMR spectrum (CDCl$_3$): 1.45 ppm (s,6H); 3.85 ppm (s,2H); 6.55 ppm (s,1H); 7–8.5 ppm (m,3H).

(c) 2-chloro 3-(4,4-dimethyl 2-oxazolinyl)pyridine 75.9 g (0.307 mole) of 2-chloro 3-(1,1-dimethyl-2-chloroethyl)aminocarbonyl pyridine and 155 g (1.84 mole) of sodium bicarbonate are placed in 2 l of toluene and the mixture is refluxed with vigorous stirring until the starting material has completely disappeared (10 to 15 hours).

The water formed by the reaction of the hydrochloric acid released with the sodium bicarbonate is collected in a separator, and the sodium chloride formed is filtered off and washed with toluene. The filtrate is then concentrated under reduced pressure to give 63.3 g of 2-chloro 3-(4,4-dimethyl 2-oxazolinyl)pyridine in the form of a yellow oil which can be purified by distillation under reduced pressure.

Yield: 63.3%.
B.p.: 110° C. (0.2 mmHg).
n$^{20}$: 1.5397.

| | Elemental analysis %: | | | |
|---|---|---|---|---|
| | C | H | N | Cl |
| Calculated | 57.02 | 5.26 | 13.30 | 16.83 |
| Found | 55.55–59.81 | 5.66–5.28 | 13.65–12.99 | 16.74–16.52 |

| I.R. spectrum (film): | |
|---|---|
| aromatic C—H | 3100–3000 cm$^{-1}$ (v.w) |
| C=N | 1650 cm$^{-1}$ (S) |
| aromatic C—C | 1575 cm$^{-1}$ (S) |

NMR spectrum (CDCl$_3$): 1.45 ppm (s,6H); 4.15 ppm (s,2H); 7–8.5 ppm (m,3H).

(d) 2-tert.butoxy 3-(4,4-dimethyl 2-oxazolinyl)pyridine 32.2 g (0.153 mole) of 2-chloro 3-(4,4-dimethyl 2-oxazolinyl)pyridine are dissolved in 90 ml of dry tetrahydrofuran. 51.4 g (0.459 mole) of potassium tert.butylate dissolved in 150 ml of dry tetrahydrofuran are then added in a manner such that the solvent is maintained at reflux by the exothermal nature of the reaction.

After being cooled, the solvent is evaporated under reduced pressure. The residue is taken up in 800 ml of diisopropylether and the solution is washed twice with 80 ml of water. After drying over sodium sulfate, the solvent is evaporated under reduced pressure to give 36 g of 2-tert.butoxy 3-(4,4-dimethyl 2-oxazolinyl)pyridine in the form of a yellow oil.

Yield: 94.7%.
n$^{20}$: 1.5047.

| | Elemental analysis %: | | |
|---|---|---|---|
| | C | H | N |
| Calculated | 67.72 | 8.12 | 11.78 |
| Found | 67.31 | 7.94 | 10.95 |

| I.R. spectrum (CHCl$_3$): | |
|---|---|
| aromatic C—H | 3100–3000 cm$^{-1}$ (s) |
| C=N | 1650 cm$^{-1}$ (S) |
| aromatic C—C | 1590 cm$^{-1}$ (S) |

NMR spectrum (CDCl$_3$): 1.3 ppm (s,6H); 1.55 ppm (s,9H); 4.10 ppm (s,2H); 6.5–8.5 ppm (m,3H).

EXAMPLE 3

Preparation of 3-(4,4-dimethyl 2-oxazolinyl) 2-methoxy pyridine (a) 2-chloro 3-(4,4-dimethyl 2-oxazolinyl)pyridine 24.7 g (0.10 mole) of 2-chloro 3-(1,1-dimethyl-2-chloroethyl)aminocarbonylpyridine, prepared as described in Example 2c, are suspended in hexamethyldisilazane and the suspension is heated at reflux for 6 h (about 125° C.). The excess hexamethyldisilazane is evaporated under reduced pressure and the residue is distilled under high vacuum to give 16.27 g of 2-chloro 3-(4,4-dimethyl 2-oxazolinyl)pyridine.

B.p.: 110° C. (0.2 mm Hg).

Spectral data identical with those in Example 2c.

(b) 3-(4,4-dimethyl 2-oxazolinyl) 2-methoxypyridine

A solution of sodium methylate is prepared by the gradual addition of 17.4 g (0.76 mole) of pieces of sodium to 210 ml of methanol which is refluxed until the solid has completely disappeared. 34.6 g (0.192 mole) of 2-chloro 3-(4,4-dimethyl 2-oxazolinyl)pyridine dissolved in 160 ml of absolute methanol are then added rapidly and the solution is refluxed for 6 hours. The excess sodium methylate is neutralized with a solution of 3M hydrogen chloride in methanol and the sodium chloride formed is filtered off. The methanol is removed under reduced pressure and the residue is taken up in dichloromethane. After the residual sodium chloride has been filtered, the solvent is evaporated to give 3-(4,4-dimethyl 2-oxazolinyl) 2-methoxypyridine in the form of a yellow oil.

Yield: 95%.

| I.R. spectrum (CHCl$_3$): | |
|---|---|
| aromatic C—H | 3100-3000 cm$^{-1}$ (s) |
| C=N | 1640 cm$^{-1}$ (S) |
| aromatic C—C | 1590 cm$^{-1}$ (S) |

| NMR spectrum (CDCl$_3$): |
|---|
| 1.4 ppm (s,6H); 4.02 ppm (s,3H); 4.07 ppm (s,2H); 6.7-7.0 ppm (m,2H); 7.9-8.4 ppm (m,2H). |

EXAMPLE 4

Preparation of 3-(4,4-dimethyl 2-oxazolinyl)2-methoxypyridine (a) 2-chloro 3-(4,4-dimethyl 2-oxazolinyl)pyridine 76.8 g (0.336 mole) of 2-chloro 3-(1,1-dimethyl 2-hydroxy-ethyl)aminocarbonylpyridine are placed in a reaction vessel immersed in a cooling bath (ice+water). 244 ml (3.36 moles) of thionyl chloride are then added in a manner such that the temperature is maintained below 20° C. Stirring is continued for 2.5 h at 20° C. and the thionyl chloride is evaporated under reduced pressure (temperature <50° C.).

2 l of toluene and 155 g (1.84 mole) of sodium bicarbonate are then added to the solution of 2-chloro 3-(1,1-dimethyl 2-chloro-ethyl)aminocarbonylpyridine thus formed and the mixture is refluxed with vigorous stirring until the starting material has completely disappeared (10 to 15 H). The water formed by the reaction of the hydrochloric acid liberated with the sodium bicarbonate is collected in a separator, and the sodium chloride formed is filtered off and washed with toluene. The filtrate is then concentrated under reduced pressure to give 2-chloro 3-(4,4-dimethyl 2-oxazolinyl)pyridine in the form of a yellow oil which can be purified by distillation under reduced pressure.

(b) 3-(4,4-dimethyl 2-oxazolinyl)2-methoxy pyridine

This compound was obtained as described in Example 3b starting from 2-chloro 3-(4,4-dimethyl 2-oxazolinyl)pyridine prepared as previously described.

Yield: 90%.

EXAMPLE 5

Preparation of 3-(4,4-dimethyl 2-oxazolinyl) 2-isopropoxy pyridine 12 g of sodium hydride (50% in oil=0.25 mole) are added during 10 minutes to 150 ml of dry tetrahydrofuran and 40 ml of isopropanol to give a suspension, the temperature of which rises to 50° C. A solution of 10.52 g (0.05 mole) of 2-chloro 3-(4,4-dimethyl 2-oxazolinyl)-pyridine in 30 ml of dry tetrahydrofuran is then added during 20 minutes and the mixture is left to stand for 1.25 hours at ambient temperature. Excess isopropanol and the tetrahydrofuran are then removed under a partial vacuum and the residue is taken up in 50 ml of water and 100 ml of diisopropyl ether. The ethereal phase is then evaporated under reduced pressure to give 12.5 g of 3-(4,4-dimethyl 2-oxazolinyl)2-isopropoxy pyridine in the form of a clear brown oil.

Yield: 95%.

| I.R. spectrum (film): | |
|---|---|
| C=N | 1640 cm$^{-1}$ |
| aromatic C—C | 1580 cm$^{-1}$ |

NMR spectrum (CDCl$_3$): 1.35 ppm (s,6H)+(d,6H); 4.1 ppm (s,2H); 5.4 ppm (m,1H); 6.7-7 ppm (m,1H); 7.9-8.4 ppm (m,2H).

EXAMPLE 6

Preparation of 3-dimethylaminocarbonyl 4-lithio 2-methoxy pyridine

A solution of 0.17 mole of lithium 2,2,6,6-tetramethyl piperidide is prepared by the addition of 0.17 mole of n-butyllithium (2.3 moles) in 74 ml of cyclohexane to 0.17 mole (28.7 ml) of 2,2,6,6-tetramethylpiperidine in 120 ml of tetrahydrofuran at a temperature below −20° C.

This solution is then added within a few minutes to a solution of 20.8 g (0.1 mole) of 3-diethylaminocarbonyl 2-methoxy pyridine and 25.65 ml (0.17 mole) of tetramethylethylenediamine in 200 ml of tetrahydrofuran cooled to −70° C. while maintaining the temperature of the solution at or below −70° C.

An orange-colored homogeneous solution of 3-diethylaminocarbonyl 4-lithio 2-methoxy pyridine is thus obtained which is used as such.

A solution of 3-diisopropylaminocarbonyl 4-lithio 2-methoxy pyridine is prepared in a similar manner.

EXAMPLE 7

Preparation of 3-diethylaminocarbonyl 4-lithio 2-methoxy pyridine 0.0375 mole of n-butyllithium (16.7 ml; 20% in cyclohexane) are added in 15 to 30 minutes to a solution of 5.2 g (0.025 mole) of 3-diethylaminocarbonyl 2-methoxy pyridine, 2.12 ml (0.0125 mole) of 2,2,6,6-tetramethyl piperidine and 5.66 ml (0.0375 mole) of tetramethylethylenediamine in 72.5 ml of tetrahydrofuran cooled to −80° C. in such a manner that the temperature is maintained below −75° C.

An orange-colored solution of 3-diethylaminocarbonyl 4-lithio 2-methoxy pyridine is thus obtained which is used as such.

A solution of 3-diisopropylaminocarbonyl 4-lithio 2-methoxy pyridine is prepared by using the same procedure as just described.

EXAMPLE 8

Preparation of 3-diethylaminocarbonyl 4-lithio 2-methoxy pyridine

Over a period of several minutes 0.0075 mole of tert-butyllithium (4.41 ml of a 1.7 molar solution in pentane) are added to a solution of 1.041 g (0.005 mole) of 3-diethylaminocarbonyl 2-methoxy pyridine and 1.13 ml (0.0075 mole) of tetramethylethylenediamine in 15 ml of tetrahydrofuran cooled to −80° C. while the temperature is maintained below −80° C. After 20 minutes at this temperature, an orange-colored solution of 3-diethylaminocarbonyl 4-lithio 3-methoxy pyridine is obtained which is used as such.

A solution of 3-diisopropylaminocarbonyl 2-methoxy pyridine is prepared in the same manner as that described above.

EXAMPLE 9

Preparation of 3-(4,4-dimethyl 2-oxazolinyl) 2-isopropoxy 4-lithio pyridine 40.8 ml (0.09 mole; 2.2 molar solution in hexane) of n-butyllithium are added to a solution of 15.20 ml (0.09 mole of 2,2,6,6-tetramethylpiperidine and 29 g (0.09 mole) of tris(dioxa-3,6 heptyl)amine in 30 ml of tetrahydrofuran cooled to a temperature below −75° C. in a manner such that the temperature remains below −70° C.

7.02 g (0.03 mole) of 3-(4,4-dimethyl 2-oxazolinyl) 2-isopropoxy pyridine dissolved in 55 ml of tetrahydrofuran are then added in 5 minutes while the temperature is maintained below −70° C. After being stirred for 20 minutes at this temperature a yellow-orange, homogeneous solution of 3-(4,4-dimethyl 2-oxazolinyl) 2-isopropoxy 4-lithio pyridine is obtained which is used as such.

A solution of 3-(4,4-dimethyl 2-oxazolinyl) 2-tert.butoxy 4-lithio pyridine is prepared in a similar manner.

EXAMPLE 10

Preparation of 3-(4,4-dimethyl 2-oxazolinyl) 2-isopropoxy 4-lithio pyridine (a) The same procedure is used as that described in Example 9 except that the solvent system tetrahydrofuran/tris.(dioxa-3,6 heptyl)amine is replaced by tetramethylethylenediamine alone or mixed with tetrahydrofuran.

A solution of 3-(4,4-dimethyl 2-oxazolinyl) 2-tert.butoxy 4-lithio pyridine is prepared in the same manner as that described above.

(b) The same procedure is used as that described in Example 9 except that the solvent system tetrahydrofuran/tris(dioxa-3,6 heptyl)amine is replaced by a tetramethylethylenediamine/tris(dioxa-3,6 heptyl)amine mixture.

A solution of 3-(4,4-dimethyl 2-oxazolinyl)2-tert.butoxy 4-lithio pyridine is prepared in the same manner as that described above.

EXAMPLE 11

Preparation of 3-diethylaminocarbonyl 4-formyl 2-methoxy pyridine

During a period of 10 to 15 minutes a reagent with electrophilic character, namely 27.8 ml (3.5 equivalents) of dimethylformamide dissolved in 20 ml of tetrahydrofuran are added to the solution of 3-diethylaminocarbonyl 4-lithio 2-methoxy pyridine obtained in Example 6 and maintained at a temperature below −70° C. The reaction mixture is poured into a solution of 57 ml of 37% hydrochloric acid in 150 ml of water and extracted 3 times with 150 ml of toluene. After drying over sodium sulfate, the solvent is evaporated under reduced pressure.

23.9 g of 3-diethylaminocarbonyl 4-formyl 2-methoxy pyridine are thus obtained in the form of a yellow oil with an aldehyde titer of 85%.

Yield: 85%.

A recrystallization in the cold or a purification by chromatography gives an analytical sample.

M.p.: <50° C. (tacky solid).

| | Elemental analysis %: | | |
|---|---|---|---|
| | C | H | N |
| Calculated | 61 | 2.83 | 11.86 |
| Found | 60.28 | 6.84 | 11.63 |

| I.R. spectrum (film): | |
|---|---|
| C=O | 1700 cm$^{-1}$ (S) aldehyde |
| C=O | 1625 cm$^{-1}$ (S) amide |
| aromatic C—C | 1570 cm$^{-1}$ (S) |

NMR spectrum (CDCl$_3$): 1.25 ppm (2t,6H); 3.0–4.0 ppm (2q,4H); 4.0 ppm (s,3H); 7.4 ppm (d,1H); 8.4 ppm (d,1H); 10.1 ppm (s,1H).

By following the same process as that described above, the following compounds have been prepared:

(a) 4-acetyl 3-diethylaminocarbonyl 2-methoxy pyridine.

| Reagent with electrophilic character: | |
|---|---|
| ethyl acetate | yield: 30% |
| acetonitrile | yield: 17% |
| N-methyl N-methoxy acetamide | yield 45% |

The product is an oil.

| I.R. spectrum (film): | |
|---|---|
| C=O | 1705 cm$^{-1}$ (S) ketone |
| C=O | 1635 cm$^{-1}$ (S) amide |
| aromatic C—C | 1590 cm$^{-1}$ (S) |

NMR spectrum (CDCl$_3$): 1.05 and 1.25 ppm (2t,6H); 2.50 ppm (s,3H); 3.15 and 3.50 ppm (2q,4H); 3.90 ppm (s,3H); 7.15 ppm (d,1H); 8.25 ppm (d,1H).

(b) 3-diethylaminocarbonyl 2-methoxy isonicotinic acid.

| Reagent with electrophilic character: | |
|---|---|
| carbon dioxide | yield: 57% |

M.p.: 145° C.

| | Elemental analysis %: | | |
|---|---|---|---|
| | C | H | N |
| Calculated | 57.13 | 6.39 | 11.10 |
| Found | 56.84 | 6.46 | 10.92 |

| I.R. spectrum (KBr): | |
|---|---|
| OH | 3500–3400 cm$^{-1}$ (m) |
| C=O | 1725 cm$^{-1}$ (S) acid |
| C=O | 1635 cm$^{-1}$ (S) amide |
| aromatic C—C | 1575 cm$^{-1}$ (S) |

NMR spectrum (CDCl$_3$/DMSOD$_6$): 0.8–1.2 ppm (m,6H); 2.8–3.8 ppm (m,4H); 3.9 ppm (s,3H); 7.35 ppm (d,1H); 8.15 ppm (d,1H).

EXAMPLE 12

Preparation of 3-diisopropylamino 4-formyl 2-methoxy pyridine

This compound was prepared according to the process described in Example 11.

| Reagent with electrophilic character: | |
|---|---|
| Ethyl formate | yield: 64.5% |

M.p.: 103°-104° C.

| I.R. spectrum (KBr): | |
|---|---|
| C=O | 1715 cm$^{-1}$ (S) aldehyde |
| C=O | 1630 cm$^{-1}$ (S) amide |
| aromatic C—C | 1570 cm$^{-1}$ (S) |

NMR spectrum (CDCl$_3$) (rotamers): 1.0–1.8 ppm (m,12H); 3.3–3.9 ppm (m,2H): 4.0 ppm (s,3H); 7.35 ppm (d,1H); 8.30 ppm (d,1H); 10.1 ppm (s,1H).

By using the same process as that described above the following compound has been prepared: 4-acetyl 3-diisopropylaminocarbonyl 2-methoxy pyridine.

| Reagent with electrophilic character: | |
|---|---|
| acetic anhydride | yield: 25–30% |
| ethyl acetate | yield: 49% |
| dimethylacetamide | yield: 15–20% |
| acetonitrile | yield: 13% |

The product is a white solid.
M.p.: 124° C.

| I.R. spectrum (KBr): | |
|---|---|
| C=O | 1700 cm$^{-1}$ (S) ketone |
| C=O | 1625 cm$^{-1}$ (S) amide |
| aromatic C—C | 1560 cm$^{-1}$ (S) |

NMR spectrum (CDCl$_3$): 1.0–1.7 ppm (m,12H); 2.5 ppm (s,3H); 3.2–3.8 ppm (m,2H); 3.9 ppm (s,3H); 7.1 ppm (d,1H); 8.2 ppm (d,1H).

EXAMPLE 12a

Preparation of 1-(1-benzenesulfonyl 5-aza 2-indolyl) 1-(3-diisopropylaminocarbonyl 2-methoxy 4-pyridyl)ethanol The experiment is carried out as in Example 12 using as reagent with electrophilic character 2-acetyl 1-benzenesulfonyl 5-aza indole.
Yield: 23%.
M.p.: 230°-232° C.

| I.R. spectrum (KBr): | |
|---|---|
| OH | 3500–3100 cm$^{-1}$ (m) |
| C=O | 1625 cm$^{-1}$ (S) |
| aromatic C—C | 1565 cm$^{-1}$ (S) |
| SO$_2$—N | (1340 cm$^{-1}$ (S) |
|  | (1175 cm (S) |

NMR spectrum (CDCl$_3$/trifluoroacetic acid) (rotamers): 1.0–1.8 ppm (m,18H); 2.0–2.2 ppm (m,3H); 3.3–3.9 ppm (m,2H); 3.95 ppm (s,3H); 6.4 ppm (m,1H); 7.0–8.7 ppm (m,10H); 9.15 ppm (s,1H).

By using the same process (1-benzylsulfonyl 5-aza 2-indolyl) (3-diisopropylaminocarbonyl 2-methoxy 4-pyridyl)methanol has been prepared.

Reagent with electrophilic character; 1-benzenesulfonyl 2-formyl 5-aza indole.
Yield: 40%.
M.p.: 234° C.

| I.R. spectrum (KBr): | |
|---|---|
| C=N | 1627 cm$^{-1}$ (S) |
| aromatic C—C | 1570 cm$^{-1}$ (S) |

NMR spectrum (CDCl$_3$/DMSOD$_6$): 0.9–1.7 ppm (m,12H); 3.1–3.9 ppm (m,3H); 3.95 ppm (s,3H); 6.5–9.0 ppm (m,11H); 9.25 ppm (s,1H).

EXAMPLE 13

Preparation of 3-(4,4-dimethyl 2-oxazolinyl) 2-isopropoxy 4-(N-methyl-N-methoxyaminocarbonyl)pyridine A reagent with electrophilic character, namely N-methoxy-N-methylcarbamoyl chloride is added during a period of 5 minutes to the solution of 3-(4,4-dimethyl 2-oxazolinyl) 2-isopropoxy 4-lithio pyridine prepared as described in Example 9 on a 0.005 molar scale and maintained at a temperature below −65° C. The temperature rises to −15° C. as a consequence of the exothermal nature of the reaction. After cooling again to −65° C. and addition of 3 ml of water, the reaction mixture is allowed to warm to 20° C. After evaporation of the solvent, the residue obtained is purified by chromatography on a column of silica gel.

3-(4,4-dimethyl 2-oxazolinyl) 2-isopropoxy 4-(N-methyl-N-methoxyaminocarbonyl)pyridine is thus obtained in the form of an oil.
Yield: 41%.

| I.R. spectrum (film): | |
|---|---|
| C=N | 1660 cm$^{-1}$ (S, broad) |
| C=O |  |
| aromatic C—C | 1575 cm$^{-1}$ (S) |

NMR spectrum (CDCl$_3$): 1.0–1.5 ppm (m,12H); 3.15 ppm (s,3H); 3.50 ppm (s,3H); 5.0–5.5 ppm (m,1H); 6.85 ppm (d,1H); 8.1 ppm (d,1H).

In the same manner as that described above were prepared:

(a) 3-(4,4-dimethyl 2-oxazolinyl) 2-isopropoxy 4-pyridine carboxylic acid.

| Reagent with electrophilic character: | |
|---|---|
| carbon dioxide | yield: 50% |

M.p.: 195° C.

| I.R. spectrum (KBr): | |
|---|---|
| OH | 3600–3300 cm$^{-1}$ (m) |
| C=O | 1700 cm$^{-1}$ (S) |
| C=N | 1660 cm$^{-1}$ (S) |
| aromatic C—C | 1570 cm$^{-1}$ (S) |

NMR spectrum (CDCl$_3$/DMSOD$_6$): 1.2–1.8 ppm (m,12H); 4.05 ppm (s,2H); 5.0–5.5 ppm (mm,2H); 7.25 ppm (d,1H); 8.2 ppm (d,1H); 9.5–10.5 ppm (broad signal, 1H).

(b) [1-dimethylaminosulfonyl 5-aza 2-indolyl] [3-(4,4-dimethyl 2-oxazolinyl) 2-isopropoxy 4-pyridyl] methanol Reagent with electrophilic character; 1-dimethylaminosulfonyl 2-formyl 5-aza indole.
Yield: 67%.
M.p.: 195° C.

| I.R. spectrum (KBr): | |
|---|---|
| OH | 3300–3000 cm$^{-1}$ |
| C=N | 1655 cm$^{-1}$ |
| aromatic C—C | 1590, 1570 cm$^{-1}$ |

NMR spectrum (CDCl$_3$+D$_2$O): 1.2–1.5 ppm (m,12H); 2.85 ppm (s,6H); 3.9 ppm (s,2H); 5.0–5.5 ppm (m,1H); 6.4–8.8 ppm (m,7H).

EXAMPLE 14

Preparation of (1-benzenesulfonyl 5-methoxy 2-indolyl) (3-diethylaminocarbonyl 2-methoxy 4-pyridyl)methanol (a) 1-benzenesulfonyl 5-methoxy indole 29.4 g (0.20 mole) of 5-methoxy indole, 20 g (0.50 mole) of powdered sodium hydroxide and 0.78 g (0.0020 mole) of tetrabutylammonium hydrogen sulfate as phase transfer catalyst are placed in 850 ml of dichloromethane and the solution is then stirred vigorously.

38.3 ml (0.30 mole) of benzenesulfonyl chloride are then added over a period of 1 hour during which a rise in temperature from 20° to 40° C. is recorded. Stirring is continued for 1 hour after the end of the addition. The excess sodium hydroxide and the sodium chloride formed are then filtered off and the filtrate is washed with water until the pH=7-8. After drying over magnesium sulfate and partial decolorization with active charcoal, the solvent is removed under reduced pressure.

51.6 g of 1-benzenesulfonyl 5-methoxy indole are thus obtained after recrystallization from ethanol.
Yield: 90%.
M.p.: 112° C.

| I.R. (KBr): | |
|---|---|
| aromatic C—H | 3140–3040 cm$^{-1}$ (M) |
| aromatic C—C | 1580–1605 cm$^{-1}$ (S) |
| SO$_2$ | 1370 cm$^{-1}$ |

NMR spectrum (CDCl$_3$): 3.7 ppm (s,3H); 6.55 ppm (d,1H); 6.7–8.0 ppm (m,9H).

(b) 1-benzenesulfonyl 2-lithio 5-methoxy indole

A solution of 0.005 mole of 1-benzenesulfonyl 5-methoxy indole, 0.0075 mole of stabilization agent and 0.0025 mole of amine in 7.6 ml of tetrahydrofuran is cooled to −70° C. 0.0075 mole of n-butyllithium are then added during 15 minutes while the temperature is maintained below −60° C. and the solution obtained is stirred for 30 minutes at this temperature.

A solution of 1-benzenesulfonyl 2-lithio 5-methoxy indole is thus obtained by using tris(dioxa-3,6 heptyl)amine as stabilization agent and 2,2,6,6-tetramethylpiperidine as amine.

The extent of metalation was estimated by proceeding as previously described in order to obtain 1-benzenesulfonyl 2-deutero 5-methoxy indole.

Extent of metalation: ≦85% (proton NMR).
NMR spectrum (CDCl$_3$): 3.7 ppm (s,3H); 6.55 ppm (s,1H); 6.8–8.0 ppm (m,8H).

(c) (1-benzenesulfonyl 5-methoxy 2-indolyl) (3-diethylaminocarbonyl 2-methoxy 4-pyridyl)methanol 1.5 equivalents of a reagent with electrophilic character in tetrahydrofuran were added during 10 to 15 minutes to the solution of 1-benzenesulfonyl 2-lithio 5-methoxy indole previously obtained and maintained at a temperature below −70° C. The reaction mixture is poured into a solution of hydrochloric acid (57 ml of 37% acid - 150 ml of water) and extracted three times with toluene. After drying over sodium sulfate, the solvent is evaporated under reduced pressure.

In this way, (1-benzenesulfonyl 5-methoxy 2-indolyl) (3-diethylaminocarbonyl 2-methoxy 4-pyridyl)methanol.

Reagent with electrophilic character: 3-diethylaminocarbonyl 4-formyl 2-methoxy pyridine.
Yield: 63%.
M.p.: 110° C.

| I.R. spectrum (KBr): | |
|---|---|
| OH | 3600–3200 cm$^{-1}$ (m) |
| C=O | 1420 cm$^{-1}$ (S) |
| aromatic C—C | 1685–1670 cm$^{-1}$ (s) |

NMR spectrum (CDCl$_3$): 0.8–1.4 ppm (m,6H); 2.8–3.8 ppm (m,5H); 3.7 ppm (s,3H); 3.9 ppm (s,3H); 6.1–8.8 ppm (m,12H).

The following compounds were prepared in the same manner as that previously described:

(1) (1-benzenesulfonyl 5-aza 2-indolyl) (3-diethylaminocarbonyl 2-methoxy 4-pyridyl)methanol Starting from 1-benzenesulfonyl 2-lithio 5-aza indole and 3-diethylaminocarbonyl 4-formyl 2-methoxy pyridine as reagent with electorphilic character, prepared according to paragraph (b) [stabilization reagent: tris(dioxa-3,6 heptyl)amine; amine: diisopropylamine]. White solid.
Yield: 74%.
M.p.: 166° C.

| | Elemental analysis %: | | | |
|---|---|---|---|---|
| | C | H | N | S |
| Calculated | 60.96 | 5.32 | 11.37 | 6.51 |
| Found | 60.96 | 5.44 | 11.31 | 6.87 |

| I.R. spectrum (KBr): | |
|---|---|
| OH | 3300–2700 cm$^{-1}$ (m, w) |
| C=O | 1620 cm$^{-1}$ (S) |
| aromatic C—C | 1590–1570 cm$^{-1}$ (M) |

NMR spectrum (CDCl$_3$+10% CF$_3$CO$_2$H): 0.8–1.4 ppm (2t,6H); 2.8–3.9 ppm (2q,4H); 3.9 ppm (s,3H); 6.5–9.2 ppm (m,12H).

(2) (1-tert.butoxycarbonyl 5-aza 2-indolyl) (3-diethylaminocarbonyl 2-methoxy 4-pyridyl)methanol Starting from 1-tert.butoxycarbonyl 2-lithio 5-aza indole and 3-diethylaminocarbonyl 4-formyl 2-methoxy pyridine as reagent with electrophilic character, prepared according to paragraph b (stabilization reagent: tetramethylethylenediamine; amine: 2,2,6,6-tetramethylpiperidine).

Purification by chromatography on silica.
Yield: 57%.
M.p.: 102° C.

| Elemental analysis %: | | | |
|---|---|---|---|
| | C | H | N |
| Calculated | 63.42 | 6.65 | 12.33 |
| Found | 62.70 | 6.69 | 11.89 |

| I.R. spectrum (KBr): | |
|---|---|
| OH | 3300–2700 cm$^{-1}$ (m) |
| C=O | 1750 cm$^{-1}$ (S) urethane |
| C=O | 1625 cm$^{-1}$ (S) |
| aromatic C—C | 1590 cm$^{-1}$ (S) |

NMR spectrum (CDCl$_3$): 0.9–1.6 ppm (m,15H); 2.8–3.9 ppm (m,5H); 3.95 ppm (s,3H); 6.5–7.4 ppm (m,4H); 8.0–8.3 ppm (m,2H); 8.8 ppm (s,1H).

EXAMPLE 15

Preparation of (1-dimethylaminosulfonyl 5-aza 2-indolyl) (3-diethylaminocarbonyl 2-methoxy 4-pyridyl)methanol (a) 1-dimethylaminosulfonyl 5-aza indole 3.84 g (0.032 mole) of 5-aza indole, 3.2 g (0.08 mole) of powdered sodium hydroxide and 0.12 g (3.6×10 mole) of tetrabutylammonium hydrogen sulfate as phase transfer catalyst are placed in 100 ml of dichloromethane and then the solution is stirred vigorously.

5 ml (0.048 mole) of dimethylaminosulfonyl chloride are then added and a rise in temperature from 20° to 40° C. is recorded. Stirring is continued for 1 hour after the end of the addition. Excess sodium hydroxide and the sodium chloride formed are then filtered off and the filtrate is washed with water until the pH=7–8.

After drying over magnesium sulfate and partial decolorization with active charcoal, the solvent is removed under reduced pressure.

A brown residue is thus obtained which is purified by chromatography on silica to give 6.1 g of 1-dimethylaminosulfonyl 5-aza indole in the form of a pale yellow solid.
Yield: 83%.
M.p.: 87° C.

| Elemental analysis %: | | | | |
|---|---|---|---|---|
| | C | H | N | S |
| Calculated | 47.99 | 4.72 | 18.65 | 14.23 |
| Found | 47.76 | 4.96 | 18.71 | 14.30 |

| I.R. spectrum (KBr): | |
|---|---|
| aromatic C—H | 3140, 3040 cm$^{-1}$ (s) |
| aromatic C—C | 1593 cm$^{-1}$ (S) |
| SO$_2$N | 1380 cm$^{-1}$ (S) |

NMR spectrum (CDCl$_3$): 2.8 ppm (s,6H); 6.7 ppm (d,1H); 7.45 ppm (d,1H); 7.8 ppm (d,1H); 8.4 ppm (d,1H); 8.9 ppm (s,1H).

(b) 1-dimethylaminosulfonyl 2-lithio 5-aza indole

A solution of 1.12 g (0.005 mole) of 1-dimethylaminosulfonyl 5-aza indole and 0.75 ml (0.005 mole) of tetramethylethylenediamine in 10 ml of tetrahydrofuran is cooled to −60° C. 0.009 mole of lithium isopropylamide (prepared by reaction of 0.009 mole of n-butyllithium with 0.009 mole of diisopropylamine in 5 ml of tetrahydrofuran at a temperature below 0° C.) are then added during a period of a few minutes in a manner such that the temperature of the medium does not exceed −40° C. The solution is then stirred at −60° C. for 30 minutes.

A solution of 1-dimethylaminosulfonyl 2-lithio 5-aza indole is thus obtained and used as such.

(c) 1-dimethylaminosulfonyl 2-formyl 5-aza indole 1.1 g (0.015 mole) of ethyl formate are added to the solution of 1-dimethylaminosulfonyl 2-lithio 5-aza indole previously obtained and the progress of the reaction is followed by thin layer chromatography. The reaction medium is neutralized by 1N hydrochloric acid and extracted with dichloromethane. After drying and evaporation of the organic phase, the residue is purified by chromatography on silica.

In this manner, 1-dimethylaminosulfonyl 2-formyl 5-aza indole is obtained in a yield of 63%.

| I.R. spectrum (film) | |
|---|---|
| C=O | 1660 cm$^{-1}$ (S) |
| N—SO$_2$ | 1390 cm$^{-1}$ (S) |

NMR spectrum (DMSOD$_6$): 3.9 ppm (s,6H); 7.8 ppm (s,1H); 8 ppm (d,1H); 8.6 ppm (d,1H); 9.2 ppm (s,1H); 10.4 ppm (s,1H).

EXAMPLE 15a

Preparation of (1-dimethylaminosulfonyl 5-aza 2-indolyl) (3-diethylaminocarbonyl 2-methoxy 4-pyridyl)methanol This compound was obtained starting from 1-dimethylaminosulfonyl 2-lithio 5-aza indole obtained in (b) in Example 15 and 3-diethylaminocarbonyl 4-formyl 2-methoxy pyridine as reagent with electrophilic character.

Purification by chromatography on silica.
Yield: 67%.
M.p.: 204° C.

| I.R. spectrum (KBr): | |
|---|---|
| OH | 3500–3000 cm$^{-1}$ (m) |
| C=O | 1630 cm$^{-1}$ (S) |
| aromatic C—C | 1590–1570 cm$^{-1}$ (S) |
| N—SO$_2$ | 1380 cm$^{-1}$ (S) |

NMR spectrum (CDCL$_3$/DMSOD$_6$): 0.7–1.4 ppm (m,6H); 2.6–3.7 ppm (m,10H); 3.9 ppm (s,3H); 5.4 ppm (s,1H); 5.6–6.2 ppm (m,1H); 7.1 ppm (d,1H); 8.1 ppm (d,1H); 8.3 ppm (d,1H); 8.7 ppm (s,1H).

EXAMPLE 16

Preparation of (1-benzenesulfonyl 5-methoxy 2-indolyl) (3-diethylaminocarbonyl 2-methoxy 4-pyridyl)methanol (a) 1-benzenesulfonyl 2-lithio 5-methoxy indole A solution of 0.15 mole of lithium 2,2,6,6-tetramethylpiperidide is prepared by the addition of 0.15 mole of n-butyllithium to 0.15 mole of 2,2,6,6-tetramethylpiperidine in 120 ml of tetrahydrofuran at a temperature lower than 20° C.

This solution is added over a period of a few minutes to a solution of 0.1 mole of 1-benzenesulfonyl 5-methoxy indole and 0.15 mole of stabilization reagent cooled to −70° C. while the temperature of the medium is maintained at or below −70° C.

A solution of 1-benzenesulfonyl 2-lithio 5-methoxy indole is thus obtained by using tris(dioxa-3,6 heptyl)amine as stabilization reagent.

(b) (1-benzenesulfonyl 5-methoxy 2-indolyl) (3-diethylaminocarbonyl 2-methoxy 4-pyridyl)methanol This compound was obtained according to the method described in Example 14c.

Reagent with electrophilic character: 3-diethylaminocarbonyl 4-formyl 2-methoxy pyridine.

Yield: 68%.

By following the same procedure as that described above the following compounds were obtained: (1) (1-tert.butoxycarbonyl 5-aza 2-indolyl) (3-diethylaminocarbonyl 2-methoxy 4-pyridyl)methanol.

Starting from 1-tert.butoxycarbonyl 2-lithio 5-aza indole and 3-diethylaminocarbonyl 4-formyl 2-methoxy pyridine as reagent with electrophilic character, prepared according to paragraph (a) (stabilization reagent: tetramethylethylenediamine).

Yield: 64%.

(2) 1-(1-benzenesulfonyl 5-aza 2-indolyl) 1-(3-diisopropylaminocarbonyl 2-methoxy 4-pyridyl)ethanol Starting from 1-benzenesulfonyl 2-lithio 5-aza indole and 4-acetyl 3-diisopropylaminocarbonyl 2-methoxy pyridine as reagent with electrophilic character, prepared according to paragraph (a) (stabilization reagent: tetramethylethylenediamine).

Yield: 37%

EXAMPLE 17

Preparation of (1-benzenesulfonyl 5-aza 2-indolyl) (3-dimethylaminocarbonyl 2-methoxy 4-pyridyl)ketone 40 g (10 equivalents of manganese dioxide are suspended in a solution of 22.7 g (0.046 mole) of (1-benzenesulfonyl 5-aza 2-indolyl) (3-diethylaminocarbonyl 2-methoxy 4-pyridyl)methanol in 400 ml of dichloromethane and the suspension is heated at reflux for 1 to 2 hours. After being cooled, the suspension is filtered and the solid is washed 4 times with 50 ml of dichloromethane. The filtrate is evaporated to dryness under reduced pressure to give a yellow solid which, on being washed with ethyl ether, becomes a cream solid.

In this manner, 19.7 g of (1-benzenesulfonyl 5-aza 2-indolyl) (3-diethylaminocarbonyl 2-methoxy 4-pyridyl)ketone are obtained.

Yield: 85%.

M.p.: 150° C.

| Elemental analysis %: | C | H | N | S |
|---|---|---|---|---|
| Calculated | 60.96 | 4.91 | 11.37 | 6.51 |
| Found | 60.87 | 4.90 | 11.42 | 6.69 |

| I.R. spectrum (KBr): | |
|---|---|
| aromatic C—H and C—H | 3100–3000 cm⁻¹ (v.w) |
| C=O ketone | 1665 cm⁻¹ (S) |
| C=O amide | 1630 cm⁻¹ (S) |
| aromatic C—C | 1590–1560 cm⁻¹ (m) |

NMR spectrum (DMSOD₆): 0.7–1.3 ppm (2t, 6H); 2.7–3.5 ppm (2q,4H); 3.9 ppm (s,3H); 7.0–9.0 ppm (m,11H).

(1-benzenesulfonyl 5-methoxy 2-indolyl) (3-diethylaminocarbonyl 2-methoxy 4-pyridyl)ketone was prepared in the same manner as that described previously but starting from (1-benzenesulfonyl 5-methoxy 2-indolyl) (3-diethylaminocarbonyl 2-methoxy 4-pyridyl)methanol.

Yield: 89%.

M.p.: 145° C.

| Elemental analysis %: | C | H | N | S |
|---|---|---|---|---|
| Calculated | 62.17 | 5.12 | 8.06 | 6.15 |
| Found | 62.32 | 5.33 | 7.82 | 6.20 |

| I.R. spectrum (KBr): | |
|---|---|
| C=O ketone | 1665 cm⁻¹ (S) |
| C=O amide | 1630 cm⁻¹ (S) |
| aromatic C—C | 1590–1560 cm⁻¹ (m) |

NMR spectrum (CDCl₃) (rotamers): 0.9–1.3 ppm (2t,6H); 3.0–3.8 ppm (2q,4H); 3.75 ppm (s,3H); 3.95 ppm (s,3H); 6.8–7.6 ppm (m,7H); 7.9–8.4 ppm (m,3H).

EXAMPLE 18

Preparation of 1-(1-benzenesulfonyl 5-aza 2-indolyl) 1-(3-diethylaminocarbonyl 2-methoxy 4-pyridyl)ethanol 0.020 mole of methyllithium (12 ml of a 1.65 molar solution in ethyl ether) are added in 5 minutes to a solution of 9.9 g (0.020 mole) of (1-benzenesulfonyl 5-aza 2-indolyl) (3-diethylaminocarbonyl 2-methoxy 4-pyridyl)ketone in 100 ml of anhydrous tetrahydrofuran, cooled to −20° C.

The solution is stirred for 10 minutes at −20° C. and then hydrolyzed with an aqueous solution of ammonium chloride (1 g/150 ml). The precipitate obtained after addition of 50 ml of ethyl ether is filtered off and the viscous solid obtained is dissolved in ethanol. The solvent is then removed under reduced pressure at 50° C.

9.26 g of 1-(1-benzenesulfonyl 5-aza 2-indolyl) 1-(3-diethylaminocarbonyl 2-methoxy 4-pyridyl)ethanol are thus obtained in the form of a white solid.

Yield: 91%.

M.p.: 236° C.

| Elemental analysis: | C | H | N | S |
|---|---|---|---|---|
| Calculated | 61.40 | 5.55 | 11.02 | 6.30 |
| Found | 59.56 | 5.49 | 10.55 | 6.33 |

| I.R. spectrum (CHCl): | |
|---|---|
| OH | 3500–3100 cm⁻¹ (m, w) |
| C=O | 1600–1620 cm⁻¹ (S) |
| aromatic C—C | 1570 cm⁻¹ (m) |

NMR spectrum (D₅-pyridine): 1.0–1.4 ppm (m,6H); 2.45 ppm (m,3H); 3.0–3.8 ppm (m,4H); 3.9 ppm (s,3H); 6.5–9.2 ppm (m,12H).

The same compound can be prepared according to the procedure just described but conducted at ambient temperature (20° C.) with methylmagnesium chloride instead of methyllithium.

EXAMPLE 19

Preparation of 1-(1-benzenesulfonyl 5-aza 2-indolyl) 1-(3-diethylaminocarbonyl 2-methoxy 4-pyridyl)ethanol (a) 1-benzenesulfonyl 2-chloromangano 5-aza indole A solution of 0.15 mole of lithium 2,2,6,6-tetramethylpiperidide is prepared by the addition of 0.15 mole of n-butyllithium to 0.15 mole of 2,2,6,6-tetramethylpiperidine in 120 ml of tetrahydrofuran at a temperature lower than −20° C. This solution is then added over a period of a few minutes to 0.1 mole of 1-benzenesulfonyl 5-aza indole cooled to −70° C. while maintaining this temperature throughout the addition. 0.15 mole of anhydrous manganous chloride is then added to the solution of 1-benzenesulfonyl 2-lithio 5-aza indole. The temperature of the medium is then brought from −65° C. to −25° C. in order to bring the exchange reaction to completion and obtain a solution of the desired manganous derivative which is used as such.

(b) 1-(1-benzenesulfonyl 5-aza 2-indolyl) 1-(3-diethylaminocarbonyl 2-methoxy 4-pyridyl)ethanol This compound was obtained according to the method described in Example 14c.

Reagent with electrophilic character: 4-acetyl 3-diethylaminocarbonyl 2-methoxy pyridine.

Yield: 45-50%.

1-(1-benzenesulfonyl 5-aza 2-indolyl) 1-(3-diisopropylaminocarbonyl 2-methoxy 4-pyridyl)ethanol was prepared in the same manner as just described but starting from 1-benzenesulfonyl 2-acetyl 5-aza indole and 3-diisopropylaminocarbonyl 4-bromomagnesium 2-methoxy pyridine, obtained from 3-diisopropylaminocarbonyl 4-lithio 2-methoxy pyridine and magnesium bromide.

Yield 30%.

EXAMPLE 20

Preparation of (1-benzenesulfonyl 5-aza 2-indolyl) (3-diethylaminocarbonyl 2-methoxy 4-pyridyl)ketone (a) 3-dimethylaminocarbonyl 2-methoxy 4-(N-methoxy N-methylaminocarbonyl) pyridine 6.3 g (0.025 mole) of 3-diethylaminocarbonyl 2-methoxy pyridine-4-carboxylic acid, 17.42 ml (0.125 mole) of triethylamine, 3.66 g (0.037 mole) of N, O-dimethylhydroxylamine hydrochloride and 16.6 g (0.037 mole) of benzotriazolyl-tris-dimethylaminophosphonium hexafluorophosphate are dissolved in 250 ml of dichloromethane and the solution is stirred at 20° C. for 5 hours. 375 ml of a saturated solution of sodium chloride are then added and the mixture is extracted three times with 250 ml of ethyl acetate. The solvent is evaporated under reduced pressure and the residue is purified by means of chromatography on silica.

In this manner, 4 g of 3-diethylaminocarbonyl 2-methoxy 4-(N-methoxy N-methylaminocarbonyl) pyridine are obtained in the form of a viscous solid.

Yield: 54%.

| I.R. spectrum (film): | |
|---|---|
| C=O | 1660-1610 cm$^{-1}$ (S, w) |

| -continued | |
|---|---|
| I.R. spectrum (film): | |
| aromatic C—C | 1590, 1570 cm$^{-1}$ (S) |

NMR spectrum (CDCl$_3$): 0.9-1.4 ppm (2t,6H); 2.7-3.6 ppm (m,4H); 3.2 ppm (s,3H); 3.6 ppm (s,3H); 3.9 ppm (s,3H); 6.8 ppm (d,1H); 8.1 ppm (d,1H).

(b) (1-benzenesulfonyl 5-aza 2-indolyl) (3-diethylaminocarbonyl 2-methoxy 4-pyridyl)ketone This compound was prepared according to the method described in Example 14c starting from 1-benzenesulfonyl 2-lithio 5-aza indole and 3-diethylaminocarbonyl 2-methoxy 4-(N-methoxy N-methylaminocarbonyl) pyridine.

Yield: 30%.

EXAMPLE 21

Preparation of (5-methoxy 2-indolyl) (3-diethylaminocarbonyl 2-methoxy 4-pyridyl)ketone 26.1 g (0.05 mole) of (1-benzenesulfonyl 5-methoxy 2-indolyl) (3-diethylaminocarbonyl 2-methoxy 4-pyridyl)ketone are dissolve in 400 ml of methanol and a solution of 27.64 g (0.2 mole) of potassium carbonate in 200 ml of water is added. The mixture is heated at 65° C. for 1 hour. After being cooled, the methanol is removed under reduced pressure and the aqueous phase is extracted twice with 300 ml of dichloromethane. The organic phase is dried over sodium sulfate and the solvents are removed under reduced pressure to give 19.6 g of crude product which is purified by chromatography.

In this manner, (5-methoxy 2-indolyl) (3-diethylamino-carbonyl 2-methoxy 4-pyridyl)ketone is obtained in a yield of 95%.

M.p.: 104° C.

| Elemental analysis %: | C | H | N |
|---|---|---|---|
| Calculated | 66.13 | 6.08 | 11.02 |
| Found | 66.08 | 6.30 | 10.78 |

| I.R. spectrum (KBr): | |
|---|---|
| NH | 3300 cm$^{-1}$ (broad) |
| C=O ketone + amide | 1630 cm$^{-1}$ (S, broad) |
| aromatic C—C | 1590-1560 cm$^{-1}$ (m) |

MNR spectrum (CDCl$_3$): 1.15 ppm (t,6H); 3.0-3.7 ppm (m,4H); 3.7 ppm (s,3H); 4.0 ppm (s,3H); 6.7-7.4 ppm (m,5H); 8.25 ppm (d,1H); 10 ppm (s,1H).

(5-aza 2-indolyl) (3-diethylaminocarbonyl 2-methoxy 4-pyridyl)ketone was prepared in the same manner as just described but starting from 2-(1-benzenesulfonyl 5-aza 2-indolyl) (3-diethylaminocarbonyl 2-methoxy 4-pyridyl)ketone.

Yield: 70% after purification by chromatography.

M.p.: 169° C.

| Elemental analysis %: | C | H | N |
|---|---|---|---|
| Calculated | 64.76 | 5.72 | 15.90 |
| Found | 64.36 | 5.87 | 15.58 |

| I.R. spectrum (KBr): | |
|---|---|
| N—H | 3300–2700 cm$^{-1}$ (broad) |
| C=O ketone + amide | 1630 cm$^{-1}$ (S, broad) |
| aromatic C—C | 1600–1550 cm$^{-1}$ (m) |

NMR spectrum (DMSOD$_6$): 1.0 ppm (2t,6H); 3.0–3.5 ppm (2q,4H); 3.9 ppm (s,3H); 7.0–9.0 ppm (m,6H); 10.5 ppm (s,1H).

EXAMPLE 22

Preparation of 6-aza 7-methoxy 3-methyl 3-(1-benzenesulfonyl 5-aza 2-indolyl)phthalide (formula VIII: X=N, R=R$_1$=CH$_3$, P'=benzenesulfonyl)

114 g (0.233 mole) of (1-benzenesulfonyl 5-aza 2-indolyl) (3-diethylaminocarbonyl 2-methoxy 4-pyridyl)ketone are dissolved in 1.2 l of anhydrous tetrahydrofuran and 19.1 g (0.256 mole) (86.8 ml of a 2.95M solution in tetrahydrofuran) of methyl magnesium chloride is added in the space of about 15 minutes while the temperature is maintained at or below 25° C.

After the mixture has been stirred for 1 hour, 146 ml of glacial acetic acid are added and the mixture is refluxed for 1.5 hours. The solvents are removed under reduced pressure and a pale yellow powder is obtained which is stirred vigorously with 460 ml of ethyl ether.

After being filtered off, 96 g of 6-aza 7-methoxy 3-methyl 3-(1-benzenesulfonyl 5-aza 2-indolyl)phthalide are obtained in the form of an off-white solid.

Yield: 95%.
M.p.: 200° C.

| Elemental analysis %: | C | H | N | S |
|---|---|---|---|---|
| Calculated | 60.68 | 3.93 | 9.65 | 7.36 |
| Found | 60.42 | 3.96 | 9.54 | 7.10 |

| I.R. spectrum (KBr): | |
|---|---|
| aromatic C—H | 3100 cm$^{-1}$ (v.w) |
| C=O | 1780 cm$^{-1}$ (S) |
| aromatic C—C | 1600 cm$^{-1}$ (S) |

NMR spectrum (CDCl$_3$): 2.2 ppm (s,3H); 4.15 ppm (s,3H); 7.0–9.0 ppm (m,11H).

The following compounds have been prepared in the same manner as that just described:

(a) 6-aza 7-methoxy 3-methyl 3-(1-benzenesulfonyl 5-methoxy 2-indolyl)phthalide starting from (1-benzenesulfonyl 5-methoxy 2-indolyl) (3-diethylaminocarbonyl 2-methoxy 4-pyridyl)ketone.

Yield 95%.
M.p.: 145° C.

| I.R. spectrum (KBr): | |
|---|---|
| C=O lactone | 1780 cm$^{-1}$ (S) |
| aromatic C—C | 1620–1590 cm$^{-1}$ (m) |

NMR spectrum (CDCl$_3$): 2.1 ppm (s,3H); 3.75 ppm (s,3H); 4.1 ppm (s,3H); 6.6–7.5 ppm (m,7H); 7.7–8.0 ppm (m,2H); 8.15 ppm (d,1H); 8.35 ppm (d,1H).

(b) 6-aza 3-(5-methoxy 2-indolyl) 7-methoxy 3-methyl phthalide starting from (5-methoxy 2-indolyl) (3-diethylaminocarbonyl 2-methoxy 4-pyridyl)ketone and 2.5 equivalents of methyl magnesium chloride.

Yield: 93%.
M.p.: 203° C.

| I.R. spectrum (KBr): | |
|---|---|
| NH | 3360 cm$^{-1}$ (broad) |
| C=O | 1765 cm$^{-1}$ (S) |
| aromatic C—C | 1615–1580 cm$^{-1}$ (m) |

NMR spectrum (DMSOD$_6$): 2.1 ppm (s,3H); 3.7 ppm (s,3H); 4.1ppm (s,3H); 6.4–7.4 ppm (m,5H); 8.45 ppm (d,1H); 10.5 ppm (s,1H).

EXAMPLE 23

Preparation of 6-aza 7-methoxy 3-(5-aza 1-benzenesulfonyl 2-indolyl)phthalide (formula VIII R=CH$_3$, R$_1$=H, X=N, P'=benzenesulfonyl)

14.8 g (0.03 mole) of (1-benzenesulfonyl 5-aza 2-indolyl) (3-diethylaminocarbonyl 2-methoxy 4pyridyl)methanol are dissolved in 233 ml of ethanol and 17.2 ml (0.3 mole) of glacial acetic acid, then the mixture at reflux for 1.5 hours. The solvents are removed under reduced pressure and a powder is obtained which is stirred vigorously with 200 ml of ethyl ether.

After being filtered off, 11.16 g of 6-aza 7-methoxy 3-(1-benzenesulfonyl 5-aza 2-indolyl)phthalide are obtained in the form of solid.

Yield: 88%.
M.p.: 177° C.

| Elemental analysis %: | C | H | N |
|---|---|---|---|
| Calculated | 59.85 | 3.59 | 9.97 |
| Found | 59.47 | 3.56 | 9.70 |

| I.R. spectrum (KBr): | |
|---|---|
| C=O | 1775 cm$^{-1}$ (S) |
| aromatic C—C | 1600 cm$^{-1}$ (S) |
| SO$_2$—N | 1375 cm$^{-1}$ (S) |
| SO$_2$ | 1325 cm$^{-1}$ (S) |

NMR spectrum (CDCl$_3$): 4.1 ppm (s,3H); 6.55 ppm (s,1H); 7.20–8.80 ppm (m,10H).

6-aza 7-methoxy 3-methyl 3-(1benzenesulfonyl 5-aza 2-indolyl)phthalide was obtained in the same manner as previously described starting from 1-(1-benzenesulfonyl 5-aza 2-indolyl) 1-(3-diethylaminocarbonyl 2-methoxy 4-pyridyl)ethanol.

EXAMPLE 24

Preparation of 6-aza 1,1-dihydro 1-hydroxy 7-methoxy 3-methyl 3-(1-benzenesulfonyl 5-aza 2-indolyl)phthalide (formula IX:X=N, R=R$_1$=CH$_3$, R'$_1$=H and P'=benzenesulfonyl)

48 g (0.11 mole) of 6-aza 7-methoxy 3-methyl 3-(1-benzenesulfonyl 5-aza 2-indolyl)phthalide are dissolved in 550 ml of anhydrous dichloromethane and the mixture is cooled to −25° C. 117.5 ml (0.176 mole) of diisobutylaluminium hydride (25% solution in toluene) are then added in 10 to 15 minutes so as to maintain the temperature of the reaction mixture between −25° C. and −20° C. After the mixture has been stirred for 30 minutes at this temperature, the excess diisobutylaluminium hydride is destroyed by addition of excess acetone and the mixture is poured into a cold solution (ice bath temperature) of 20% acetic acid. The aqueous phase is extracted with 300 ml of dichloromethane, the pooled organic phases are dried over sodium sulfate and the solvent is removed under reduced pressure to give 48.2 g of a residue. This residue is suspended in 480 ml of diisopropyl ether, stirred for 30 minutes and filtered off.

46.6 g of 6-aza 1,1-dihydro 1-hydroxy 7-methoxy 3-methyl 3-(1-benzenesulfonyl 5-aza 2-indolyl)phthalide are thus obtained in the form of a pale yellow powder.
Yield: 97%.
M.p.: decomposes at about 250° C.

| Elemental analysis %: | C | H | N | S |
|---|---|---|---|---|
| Calculated | 60.40 | 4.38 | 9.61 | 7.33 |
| Found | 60.23 | 4.37 | 9.52 | 7.46 |

| I.R. spectrum (KBr): | |
|---|---|
| OH | 3200–2700 cm$^{-1}$ (m, w) |
| aromatic C—C | 1610 cm$^{-1}$ (S) |
| C—O—C | 1175 cm$^{-1}$ (S) |

NMR spectrum (DMSOD$_6$): 2.10 ppm (s,3H); 4.0 ppm (s,3H); 6.4–9.0 ppm (m,13H).

6-aza 1,1-dihydro 1-hydroxy 7-methoxy 3-methyl 3-(1-benzenesulfonyl 5-methoxy 2-indolyl)phthalide was obtained in the same manner as previously described starting from 6-aza 7-methoxy 3-methyl 3-(1-benzenesulfonyl 5-methoxy 2-indolyl)phthalide.
Yield: 95%.
M.p.: 170° C.

| I.R. spectrum (KBr): | |
|---|---|
| OH | 3600–3300 cm$^{-1}$ (broad) |
| aromatic C—C | 1620–1580 cm$^{-1}$ (m) |

NMR spectrum (CDCl$_3$) (rotamers): 2.05 and 2.15 ppm (2s,3H); 3.70 and 3.75 ppm (2s,3H); 4.0 and 4.05 ppm (2s,3H); 6.4 and 8.3 ppm (m,13H).

EXAMPLE 25

Preparation of 6-aza 1,1-dihydro 1-hydroxy 7-methoxy 3-(1-benzenesulfonyl 5-aza 2-indolyl)phthalide (formula IX:X=N, R$_1$=R'$_1$=H, R=CH$_3$, P'=benzenesulfonyl)

46.3 g (0.11 mole) of 6-aza 7-methoxy 3-(1-benzenesulfonyl 5-aza 2-indolyl)phthalide are dissolved in 550 ml of anhydrous dichloromethane and the mixture is cooled to −25° C. 161.5 ml (0.242 mole) of diisobutylaluminium hydride are added in 10 to 15 minutes so as to maintain the temperature of the reaction mixture at or below −70° C. After the mixture has been stirred for 30 minutes at this temperature, the excess diisobutylaluminium hydride is destroyed by the addition of excess acetone and the mixture is poured into an ice-cold solution of 20% acetic acid. The aqueous phase is extracted with 300 ml of dichloromethane, the organic phases are pooled and dried over sodium sulfate. The solvent is removed under reduced pressure and the residue obtained is suspended in 480 ml of diisopropyl ether. The suspension is stirred for 30 minutes and filtered.

6-aza 1,1-dihydro 1-hydroxy 7-methoxy 3-(5-aza 1-benzenesulfonyl 2-indolyl)phthalide is thus obtained.

Yield: 85%.
M.p: 213° C.

| I.R. spectrum (KBr): | |
|---|---|
| OH | 3200–2700 cm$^{-1}$ |
| C=O | 1715 cm$^{-1}$ |
| aromatic C—C | 1595 cm$^{-1}$ |
| C—O—C | 1165 cm$^{-1}$ |

NMR spectrum (DMSOD$_6$/CF$_3$CO$_2$H; 9/1): 4.0 ppm (s,3H); 6.5–9.5 ppm (m,13H).

EXAMPLE 26

Preparation of 6-aza 1,1-dihydro 1,3-dimethyl 1-hydroxy 7-methoxy 3-(1-benzenesulfonyl 5-aza 2-indolyl)phthalide (formula IX:X=N, R=R$_1$=R'$_1$=CH$_3$, P'benzenesulfonyl)

48 g (0.11 mole) of 6-aza 7-methoxy 3-methyl 3-(1-benzenesulfonyl 5-aza 2-indolyl)phthalide are dissolved in 550 ml of anhydrous tetrahydrofuran and the mixture is cooled to −40° C. 18.1 g (0.242 mole) of methylmagnesium chloride are then added in 10 to 15 minutes so as to maintain the temperature of the reaction mixture at −40° C. The mixture is stirred and the temperature is allowed to rise to 0° C., then the excess of methylmagnesium chloride is destroyed by the addition of acetone in excess and the mixture is poured into an ice-cold solution of 20% acetic acid. The aqueous phase is extracted with 300 ml of dichloromethane, the organic phases are pooled and dried over sodium sulfate. The solvent is removed under reduced pressure and the residue obtained is suspended in 480 ml of diisopropyl ether. The suspension is stirred for 30 minutes and filtered.

6-aza 1,1-dihydro 1,3-dimethyl 1-hydroxy 7-methoxy 3-(1-benzenesulfonyl 5-aza 2-indolyl)phthalide is thus obtained.
Yield: 85%.
M.p: about 195° C. (descomposition).

| I.R. spectrum (KBr): | |
|---|---|
| OH | 3600–3000 cm$^{-1}$ (m, w) |
| aromatic C—C | 1610 cm$^{-1}$ (S) |
| C—O—C | 1180 cm$^{-1}$ (S) |
| SO$_2$—NC | 1370 cm$^{-1}$ (S) |
| | 1180 cm (S) |

NMR spectrum (DMSOD$_6$): 1.35, 1.80, 2.05 and 2.15 ppm (4s,6H); 3.0 and 3.5 ppm (m,1H); 3.95 ppm (s,3H); 6.3–8.8 ppm (m,11H).

The following compounds were obtained in the same manner as that just described:

(a) 6-aza 1,1-dihydro 1,3-dimethyl 1-hydroxy 7-methoxy 3-(1-benzenesulfonyl 5-methoxy 2-indolyl)phthalide starting from 6-aza 7-methoxy 3-methyl 3-(1-benzenesulfonyl 5-methoxy 2-indolyl)phthalide and 2 equivalents of methyl magnesium chloride, the reaction taking place at a temperature varying from −30° C. to +20° C.
Yield: 85%.
M.p.: 158° C.

| I.R. spectrum (KBr): | |
|---|---|
| OH | 3540–3460 cm$^{-1}$ (broad) |

| I.R. spectrum (KBr): | |
|---|---|
| aromatic C—C | 1620-1580 cm$^{-1}$ (m) |

NMR spectrum (CDCl$_3$): 1.9-2.2 ppm (m,6H); 3.2-3.6 ppm (m,1H); 3.65 ppm (s,3H); 4.0 ppm (s,3H); 6.2-8.3 ppm (m,11H).

(b) 6-aza 1,1-dihydro 3-(5-methoxy 2-indolyl) 7-methoxy phthalide starting from 6-aza 3-(5-methoxy 2-indolyl) 3-methyl 7-methoxy phthalide and 3 equivalents of methylmagnesium chloride, the reaction taking place at a temperature between −40° C. and +20° C.

Yield: 80%.
M.p.: about 86° C.

| I.R. spectrum (KBr): | |
|---|---|
| N—H | 3500-3300 cm$^{-1}$ (broad) |
| aromatic C—C | 1630-1580 cm$^{-1}$ (m) |

NMR spectrum (DMSOD$_6$): 1.8-2.0 ppm (m,6H); 3.7 ppm (s,3H); 6.2-7.4 ppm (m,6H); 8.1 ppm (dd,1H); 10.4 and 10.6 ppm (2s,1H).

EXAMPLE 27

Preparation of 6-aza 1,1-dihydro 1-hydroxy 7-methoxy 3-(5-aza 2-indolyl)phthalide (formula IX: X=N, R$_1$=R$'_1$=P'H, R=CH$_3$)

(a) 6-aza 1,1-dihydro 1,7-dimethoxy 3-(1-benzenesulfonyl 5-aza 2-indolyl)phthalide 14.24 g (0.036 mole) of 6-aza 1,1-dihydro 1-hydroxy 7-methoxy 3-(1-benzenesulfonyl 5-aza 2-indolyl)phthalide are suspended in 276 ml of anhydrous methanol, then 7.8 ml (0.063 mole) of boron trifluoride etherate are added. The homogeneous solution is then stirred for 4 hours. The reaction mixture is poured slowly into a cold aqueous solution of sodium bicarbonate (32 g/900 ml of ice-cold water). The precipitate formed is filtered off and dried under reduced pressure at 50° C.

12.6 g of 6-aza 1,1-dihydro 1,7-dimethoxy 3-(1-benzensulfonyl 5-aza 2-indolyl)phthalide are thus obtained in the form of an off-white powder.

Yield: 80%.
M.p.: 110° C. (unclear melt).

| I.R. spectrum (KBr): | |
|---|---|
| aromatic C—C | 1605, 1595 cm$^{-1}$ (S) |
| SO$_2$—N | 1375 cm$^{-1}$ (S) |
|  | 1170 cm (S) |

NMR spectrum (DMSOD$_6$): 3.3 and 3.5 ppm (2s,3H); 4.0 ppm (s,3H); 6.3-9.0 ppm (m,13H).

6-aza 1,1-dihydro 1,7-dimethoxy 1,3-dimethyl 3-(1-benzenesulfonyl 5-aza 2-indolyl)phthalide was prepared in the same manner as that previously described but starting from 6-aza 1,1-dihydro 1,3-dimethyl 1-hydroxy 7-methoxy 3-(1-benzenesulfonyl 5-aza 2-indolyl)phthalide.

Yield: 69%.
M.p.: 218° C.

| I.R. spectrum: | |
|---|---|
| aromatic C—C | 1605-1590 cm$^{-1}$ (S) |
| C—O—C | 1180 cm$^{-1}$ (S) |

| I.R. spectrum: | |
|---|---|
| SO$_2$N | 1170 cm$^{-1}$ (S) |

NMR spectrum (CDCl$_3$/DMSOD$_6$: 2/1) (mixture of enantiomers): 1.8, 2.10, 2.15 and 2.20 ppm (4s,6H); 3.15 and 3.30 ppm (2s,3H); 4.0 ppm (s,3H); 6.4-8.8 ppm (m,11H).

(b) 6-aza 1,1-dihydro 1,7-dimethoxy 3-(5-aza 2-indolyl)phthalide

An aqueous solution of 22.25 g (0.161 mole) of potassium bicarbonate in 86 ml of water is added over a period of a few minutes to a solution of 10.06 g (0.023 mole) of 6-aza 1,1-dihydro 1,7-dimethoxy 3-(1-benzenesulfonyl 5-aza 2-indolyl)phthalide in 207 ml of methanol. The suspension obtained is stirred at 20° C. for 4 hours to give a clear solution. The solution is concentrated under reduced pressure and the residue is taken up in 144 ml of dichloromethane and 58 ml of water. The organic phase is filtered rapidly through silica, the silica is rinsed with methanol and the filtrate is concentrated under reduced pressure.

5.41 g of 6-aza 1,1-dihydro 1,7-dimethoxy 3-(5-aza 2-indolyl)phthalide are thus obtained in the form of a pale yellow solid.

Yield: 79%.
M.p.: about 135° C. (decomposition).

| I.R. spectrum (KBr): | |
|---|---|
| N—H | 3400-3300 cm$^{-1}$ (m) |
| aromatic C—C | 1610, 1595 cm$^{-1}$ (S) |
| C—O—C | 1080 cm$^{-1}$ (S) |

NMR spectrum (CDCl$_3$) (mixture of enantiomers): 3.5 and 3.7 ppm (2s,3H); 3.85 and 4.0 ppm (2s,3H); 6.0-7.4 ppm (m,5H); 8.0-8.20 ppm (m,2H); 8.8 ppm (s,1H); 9.8-10.5 ppm (m,1H).

(c) 6-aza 1,1-dihydro 1-hydroxy 7-methoxy 3-(5-aza 2-indolyl)phthalide 3 g (0.010 mole) of 6-aza 1,1-dihydro 1,7-dimethoxy 3-(5-aza 2-indolyl)phthalide are dissolved in 100 ml of acetone and 1 ml of water, then 5 ml (0.041 mole) of boron trifluoride etherate are added. After being stirred for 48 hours at 20° C. the mixture is neutralized with an aqueous solution of sodium bicarbonate (6.88 g/7 ml of water). After evaporation of the solvents under reduced pressure, the residue is taken up in a dichloromethane/water (1/1) mixture. The precipitate obtained is filtered off and dried under a partial vacuum.

2.20 g of 6-aza 1,1-dihydro 1-hydroxy 7-methoxy 3-(5-aza 2-indolyl)phthalide are thus obtained in the form of a yellow solid.

Yield: 78%.
M.p.: >250° C. (decomposition).

| I.R. spectrum (KBr): | |
|---|---|
| OH | 3600-3100 cm$^{-1}$ (m, w) |
| aromatic C—C | 1605, 1580 cm$^{-1}$ (S) |
| C—O—C | 1080 cm$^{-1}$ (S) |

NMR spectrum (DMSOD$_6$): 4.0 ppm (s,3H); 6.0-9.3 ppm (m,10H).

EXAMPLE 28

Preparation of 6-aza 1,1-dihydro 1-hydroxy 7-methoxy 3-methyl 3-(5-aza 2-indolyl)phthalide (formula IX: X=N, R=R$_1$=CH$_3$, P'=R'$_1$=H).

(a) 6-aza 1,1-dihydro 1,7-dimethoxy 3-methyl 3-(5-aza 1-benzenesulfonyl 2-indolyl)phthalide This compound was obtained according to the procedure of Example 27 starting from 6-aza 1,1-dihydro 1-hydroxy 1-methoxy 3-methyl 3-(1-benzenesulfonyl 5-aza 2-indolyl)phthalide.

Yield: 78%.

M.p.: 167° C. (not sharp).

| I.R. spectrum (KBr): | |
|---|---|
| aromatic C-13 C | 1610, 1595 cm$^{-1}$ (S) |
| SO$_2$—N | 1380 cm$^{-1}$ |
| C—O—C | 1190 cm$^{-1}$ (S) |
| SO$_2$—N | 1175 cm$^{-1}$ (S) |

NMR spectrum (CDCl$_3$): 2.1 ppm (s,3H); 3.5 ppm (s,3H); 4.0 ppm (s,3H); 6.0–9.0 ppm (m,12H).

(b) 6-aza 1,1-dihydro 1,7-dimethoxy 3-methyl 3-(5-aza 2-indolyl)phthalide.

An aqueous solution of 0.092 mole of potassium bicarbonate in 86 ml of water is added, over a period of a few minutes, to a solution of 10.3 g (0.023 mole) of 6-aza 1,1-dihydro 1,7-dimethoxy 3-(1-benzenesulfonyl 5-aza 2-indolyl)phthalide in 207 ml of methanol. The suspension is stirred at reflux for 2 hours to give a clear solution.

The solution is concentrated under reduced pressure and the residue is taken up in 144 ml of dichloromethane and 58 ml of water. The organic phase is filtered rapidly through silica, the silica is rinsed with methanol, the filtrate is concentrated under reduced pressure and purified by chromatography on silica.

6-aza 1,1-dihydro 1,7-dimethoxy 3-methyl 3-(5-aza 2-indolyl)phthalide is thus obtained.

Yield: 80%.

M.p.: 121° C. (not sharp).

| Elemental analysis: | | | |
|---|---|---|---|
| | C | H | N |
| Calculated | 65.58 | 5.50 | 13.50 |
| Found | 63.85 | 5.47 | 12.95 |

| I.R. spectrum (KBr): | |
|---|---|
| N—H | 3500–3300 cm$^{-1}$ (m, w) |
| aromatic C—C | 1610, 1595 cm$^{-1}$ (S) |
| C—O—C | 1070 cm$^{-1}$ (S) |

NMR spectrum (CDCl$_3$) (mixture of enantiomers): 2.0 and 2.1 ppm (2s,3H); 3.5 and 3.7 ppm (2s,3H); 3.8 and 4.0 ppm (2s,3H); 6.0–9.0 ppm (m,7H); 9.5–10 ppm (m,1H).

(c) 6-aza 1,1-dihydro 1-hydroxy 7-methoxy 3-methyl 3-(5-aza 2-indolyl)phthalide

A solution of 3 g (0.009 mole) of 6-aza 1,1-dihydro 1,7-dimethoxy 3-methyl 3-(5-aza 2-indolyl)phthalide in 46 ml of 0.05M hydrochloric acid (0.015 mole) is stirred at 20° C. for 3 hours and then neutralized with 1.94 g of sodium bicarbonate. The aqueous phase is reduced to 10 ml by evaporation under reduced pressure and cooled in ice in order to bring the precipitation of the product to completion. The precipitate is filtered off and dried by washing with ethyl ether.

2.6 g of 6-aza 1,1-dihydro 1-hydroxy 7-methoxy 3-methyl 3-(5-aza 2-indolyl)phthalide are thus obtained in the form of a white solid.

Yield: 90%.

M.p.: about 210° C. (decomposition).

| I.R. spectrum (KBr): | |
|---|---|
| NH, OH | 3600–3100 cm$^{-1}$ (m, w) |
| aromatic C—C | 1600–1580 cm$^{-1}$ (S) |
| C—O—C | 1080 cm$^{-1}$ (S) |

NMR spectrum (D$_5$-pyridine): 2.3 ppm (s,3H); 4.1 ppm (s,3H); 5.5–6.5 ppm (m,2H); 7.0–0.5 ppm (m,7H).

NMR spectrum (DMSOD$_6$): 1.9 ppm (s,3H); 4.1 ppm (s,3H); 5.5–6.5 ppm (m,2H); 6.5–9.0 ppm (m,7H).

EXAMPLE 29

Preparation of 6,11-dihydro 6,11-dihydroxy 10-methoxy 6-methyl 5H-pyrido[3',4':4,5]pyrrolo[2,3-g]isoquinoline (formula XXVII: R=R$_1$=CH$_3$, R'$_1$=H)

47 ml (0.47 mole) of 10N sodium hydroxide are added during a period of 5 minutes to a solution of 41.12 g (0.094 mole) of 6-aza 1,1-dihydro 1-hydroxy 7-methoxy 3-methyl 3-(1-benzenesulfonyl 5-aza 2-indolyl)phthalide in 200 ml of methanol cooled to 0° C., then the suspension is stirred for 2.5 hours at about 20° C. to give rise to a homogeneous brown solution. After a further hour of stirring, the expected product precipitates. Precipitation is then brought to completion by cooling in ice for one hour. The precipitate is filtered off and dried under a partial vacuum. 26.7 g of 6,11-dihydro 6,11-dihydroxy 10-methoxy 6-methyl 5H-pyrido[3',4':4,5]-pyrrolo[2,3-g]isoquinoline are obtained in the form of an off-white powder.

Yield: 86%.

M.p.: about 190° C.

The proton NMR shows that the product forms a solvate with methanol in the constant ratio of 1/1.

| I.R. spectrum (KBr): | |
|---|---|
| NH | 3500–3400 cm$^{-1}$ (m) |
| OH | 3300–3100 cm$^{-1}$ (m) |
| aromatic C—C | 1620, 1595, 1570 cm$^{-1}$ (m) |

NMR spectrum (D$_5$-pyridine): 2.1 ppm (s,3H); 3.35 ppm (s,3H); 4.1 ppm (s,3H); 4.8–5.5 ppm (1m,4H); 6.2 ppm (s,1H); 7.5–7.9 ppm (2d,3H); 8.3–8.7 ppm (2d,2H); 9.4 ppm (s,1H).

EXAMPLE 30

Preparation of 6,11-dihydro 6,11-dihydroxy 6,11-dimethyl 10-methoxy 5H-pyrido[3',4':4,5]pyrrolo[2,3-g]isoquinoline (formula XXVII: R=R$_1$=R'$_1$=CH$_3$)

47 ml (0.47 mole) of 10N sodium hydroxide are added in 5 minutes to a solution of 42.24 g (0.094 mole) 6-aza 1,1-dihydro 1,3-dimethyl 1-hydroxy 7-methoxy 3-(1-benzenesulfonyl 5-aza 2-indolyl)phthalide in 200 ml of methanol cooled to 0° C., then the suspension is stirred for 8 hours at 20° C. which leads to the precipitation of the expected product. Precipitation is then brought to completion by cooling in ice for 1 hour. The precipitate is filtered off and dried under a partial vacuum. The product is then purified by chromatography on silica.

6,11-dihydro 6.11-dihydroxy 6,11-dimethyl 10-methoxy 5H-pyrido[3',4':4,5]pyrrolo[2,3-g]isoquinoline is thus obtained.

Yield: 73%.
M.p.: >250° C.

| I.R. spectrum (KBr): | |
|---|---|
| OH, NH | 3700–3000 cm$^{-1}$ (m, w) |
| aromatic C—C | 1600 cm$^{-1}$ (S, 1) |

NMR spectrum (D$_5$-pyridine): mixture of enantiomers 1.8–2.3 ppm (m,6H); 3.9–4.0 ppm (m,3H); 6.5–9.2 ppm (m,3H).

EXAMPLE 31

Preparation of 6,11-dihydro 6,11-dihydroxy 10-methoxy 5H-pyrido[3',4':4,5]pyrrolo[2,3-g]isoquinoline (formula XXVII: R=CH$_3$, R$_1$=R'$_1$=H)

10 ml (0.10 mole) of 10N sodium hydroxide are added in 5 minutes to a solution of 26.6 g (0.094 mole) of 6-aza 1,1-dihydro 1-hydroxy 7-methoxy 3-(5-aza 2-indolyl)phthalide in 200 ml of methanol cooled to 0° C., then the suspension is stirred for 3.5 hours at 20° C. which leads to the precipitation of the expected product. Precipitation is then brought to completion by cooling in ice for one hour. The precipitate is filtered off and dried under a partial vacuum.

6,11-dihydro 6,11-dihydroxy 10-methoxy 5H-pyrido[3',4':4,5]pyrrolo[2,3-g]isoquinoline is thus obtained.

Yield: 41%.
M.p.: >260° C. (decomposition).

| I.R. spectrum (KBr): | |
|---|---|
| OH. NH | 3600–3000 cm$^{-1}$ (m, w) |
| aromatic C—C | 1665–1580 cm$^{-1}$ (S) |

NMR spectrum (DMSOD$_6$+D$_5$-pyridine: 1/1): 4.1 ppm (s,3H); 7.0–9.3 ppm (m,10H).

EXAMPLE 32

Preparation of 6,11-dihydro 6,11-dihydroxy 10-methoxy 6-methyl 5H-pyrido[3',4':4,5]pyrrolo[2,3-g]isoquinoline (formula XXVII: R=R$_1$=CH$_3$, R'$_1$=H)

The same procedure was used as that described in Example 29 starting from 6-aza 1,1-dihydro 1-hydroxy 7-methoxy 3-methyl 3-(5-aza 2-indolyl)phthalide and 1 equivalent of 10N sodium hydroxide.
Yield: 78.5%.

EXAMPLE 33

Preparation of 10-methoxy 6-methyl 5H-pyrido[3',4':4,5]pyrrolo[2,3-g]isoquinoline (formula X: R=R$_1$=CH$_3$, R'$_1$=H, X=N)

12.02 g (0.036 mole) of 6,11-dihydro 6,11-dihydroxy 10-methoxy 6-methyl 5H-pyrido[3',4':4,5]pyrrolo[2,3-g]isoquinoline and 3.45 g (0.092 mole) of sodium borohydride are dissolved in 97 ml of peroxide-free dimethyl ether of diethylene glycol and heated to 120°–130° C. for 20 to 30 minutes. The mixture is cooled in an ice bath and 27 ml of acetone are added to destroy the excess sodium borohydride. 600 ml of 2N hydrochloric acid are then introduced during a period of 15 minutes while the temperature is maintained at or below 10° C. and then the mixture is stirred for 4 hours at ambient temperature. The mixture is poured into 275 ml of a pre-cooled 35% sodium hydroxide solution and the mixture is stirred for one hour. The precipitate formed is filtered off and then dried under a partial vacuum at 50° C.

9.34 g of 10-methoxy 6-methyl 5H-pyrido[3',4':4,5]pyrrolo[2,3-g]isoquinoline are thus obtained in the form of a greenish white powder.

Yield: 97%.
M.p.: >263° C.

| | Elemental analysis % (corresponding to the hemihydrate: ½ HO): | | |
|---|---|---|---|
| | C | H | N |
| Calculated | 70.59 | 5.15 | 15.44 |
| Found | 70.65 | 4.91 | 15.28 |

| I.R. spectrum (KBr): | |
|---|---|
| NH | 3300–2500 cm$^{-1}$ (m, w) |
| C=N, C=C | 1640 cm$^{-1}$ (s) |
| | 1610 cm$^{-1}$ (S) |
| aromatic C—C | 1585 cm$^{-1}$ (S) |

NMR spectrum (trifluoroacetic acid): 3.2 ppm (s,1H); 4.90 ppm (s,3H); 8.0–8.5 ppm (m,3H); 8.6–9.2 ppm (m,1H); 9.4–10.1 ppm (m,2H).

10-methoxy 5H-pyrido[3',4':4,5]pyrrolo[2,3-g]isoquinoline has been prepared in the same manner as that just described but starting from 6,11-dihydro 6,11-dihydroxy 5H-pyrido[3',4':4,5]pyrrolo[2,3-g]isoquinoline.

Yield: 83%.

NMR spectrum (trifluoroacetic acid): 4.5 ppm (s,3H); 6.7–7.0 ppm (m,2H); 7.7–8.6 ppm (m,4H); 8.9 ppm (d,1H).

EXAMPLE 34

Preparation of 1,9-dimethoxy 5-methyl 6H-pyrido[4,3-b]carbazole (formula X: R=R$_1$=CH$_3$, R'$_1$=H, X=C—OCH$_3$)

A solution of 4.77 g (0.085 mole) of potassium hydroxide pellets in 10 ml of methanol is added during a period of 5 minutes to a suspension of 3.97 g (0.0085 mole) of 6-aza 1,1-dihydro 1-hydroxy 7-methoxy 3-methyl 3-(1-benzenesulfonyl 5-methoxy 2-indolyl)phthalide in 20 ml of methanol and the mixture is refluxed for 1 hour.

The reaction mixture is diluted by the addition of 70 ml of methanol and cooled in an ice bath. The precipitate obtained is filtered off and dried under reduced pressure to give 1.59 g of product. A second crop of 0.277 g is obtained by evaporating the filtrate to dryness and by chromatographing the residue on silica (solvent: ethyl acetate/hexane).

In this manner, 1.767 g of 1,9-dimethoxy 5-methyl 6H-pyrido[4,3-b]carbazole are obtained.

Yield: 71%.

| I.R. spectrum (KBr): | |
|---|---|
| NH | 3400–3300 cm$^{-1}$ (broad) |
| C—C and C=C | 1640–1590 cm$^{-1}$ (m) |

NMR spectrum (DMSOD$_6$): 2.8 ppm (s,3H); 3.9 ppm (s,3H); 4.10 ppm (s,3H); 7.1 ppm (dd,1H, J=9 Hz, J'=2.5 Hz); 7.45 ppm (d,1H, J=9 Hz); 7.50 ppm (d,1H, J''=6.5 Hz); 7.9 ppm (d,1H, J''=6.5 Hz); 7.95 ppm (d,1H, J'=2.5 Hz); 8.9 ppm (s,1H); 11.15 ppm (s,1H).

EXAMPLE 35

Preparation of 10-methoxy 6-methyl 5H-pyrido[3',4':4,5]pyrrolo[2,3-g]isoquinoline (formula X: R=R$_1$=CH$_3$, R'$_1$=H, X=N)

10.937 g (0.025 mole) of 6-aza 3-(1-benzenesulfonyl 5-aza 2-indolyl) 1,1-dihydro 1-hydroxy 7-methoxy 3-methyl phthalide and 14.03 g of potassium hydroxide pellets are placed in 80 ml of ethanol and heated at reflux for 2 hours. The solvent is evaporated to dryness in a vacuum, the residue is taken up in 100 ml of water and the suspension obtained is filtered. The solid collected is taken up in 50 ml of water and the suspension is stirred for 15 hours.

After filtration and drying in a vacuum, 5.576 g of 10-methoxy 6-methyl 5H-pyrido[3',4':4,5]pyrrolo[2,3-g]isoquinoline are obtained in the form of a brown powder.

Yield: 85%.

Same analytical data as for Example 33.

EXAMPLE 36

Preparation of 5,11-dihydro 1,9-dimethoxy 5-hydroxy 5-methyl 11-methylene 6H-pyrido[4,3-b]carbazole (formula XXVIII: R=R$_1$=R$_2$=CH$_3$, R$_{14}$=H)

2.04 g (0.006 mole) of 6-aza 1,1-dihydro 1,3-dimethyl 1-hydroxy 7-methoxy 3-(5-methoxy 2-indolyl)phthalide are placed in 9 ml of methanol and 2.4 ml of water. 18 ml of potassium hydroxide (5N solution in methanol) are added and the mixture is heated for 3 to 4 hours between 40° and 45° C. After cooling and addition of 36 ml of water, the precipitate obtained is filtered off and dried under reduced pressure.

1.55 g of 5,11-dihydro 1,9-dimethoxy 5-hydroxy 5-methyl 11-methylene 6H-pyrido[4,3-b]carbazole are thus obtained.

Yield: 80%.

M.p.: about 208° C.

| I.R. spectrum (KBr): | |
|---|---|
| OH, NH | 3460, 3360 cm$^{-1}$ |
| exocyclic C=C | 1615 cm$^{-1}$ |
| aromatic C—C | 1580 cm$^{-1}$ |

NMR spectrum (CD$_3$OD/DMSOD$_6$:2/1):
1.65 ppm (s,3H); 3.80 ppm (s,3H); 4.0 ppm (s,3H); 6.0 ppm (d,1H); 6.45 ppm (d,1H); 6.8 ppm (dd,1H); 7.2–7.5 ppm (m,3H); 8.1 ppm (d,1H).

EXAMPLE 37

Preparation of 1,9-dimethoxy 5,11-dimethyl 6H-pyrido[4,3-b]carbazole (formula X: R=R$_1$=R'$_1$=CH$_3$, X=C—OCH$_3$)

0.322 g (0.001 mole) of 5,11-dihydro 1,9-dimethoxy 5-hydroxy 5-methyl 11-methylene 6H-pyrido[4,3-b]carbazole and 0.19 g (0.005 mole) of sodium borohydride are dissolved in 5 ml of peroxide-free dimethyl ether of diethylene glycol and heated to 120°–130° C. for 20 to 30 minutes. The mixture is cooled in an ice bath and 1 ml of acetone is added to destroy the excess sodium borohydride. 15 ml of 2N hydrochloric acid are then introduced during 15 minutes at a temperature equal to or lower than 10° C. and the mixture is stirred for 4 hours at ambient temperature. The mixture is poured into 8 ml of a pre-cooled 35% sodium hydroxide solution and the mixture is stirred for 1 hour. The precipitate formed is filtered off and dried in a partial vacuum at 40° C.

0.254 g of 1,9-dimethoxy 5,11-dimethyl 6H-pyrido[4,3-b]carbazole are thus obtained.

Yield: 83%.

M.p.: about 190° C.

| I.R. spectrum (KBr): | |
|---|---|
| NH | 3380 cm$^{-1}$ |
| C—C and C=C | 1595 cm$^{-1}$ |

NMR spectrum (DMSOD$_6$): 2.7 ppm (s,3H); 3.3 ppm (s,3H); 3.9 ppm (s,3H); 4.1 ppm (s,3H); 6.5–8 ppm (m,5H); 11 ppm (m,1H).

EXAMPLE 38

Preparation of 10-(3-diethylamino-propylamino) 6-methyl 5H-pyrido[3',4':4,5]pyrrolo[2,3-g]isoquinoline (formula I: Am=3-diethylamino-propylamino: R$_1$=CH$_3$, R'$_1$=H, X=N)

10.53 g (0.040 mole) of 10-methoxy 6-methyl 5H-pyrido[3',4':4,5]pyrrolo[2,3-g]isoquinoline are placed in a mixture of 130 ml (0.824 mole) of diethylaminopropylamine and 12.2 ml of a methanolic solution of hydrogen chloride (6.54N; 0.080 mole). The mixture is gradually heated up to the reflux temperature of the amine, during which time the methanol is distilled. The reaction mixture is then maintained between 150° and 160° C. for 5 to 6 hours. Excess amine is distilled under reduced pressure, the residue is taken up in 250 ml of water and neutralized by the addition of 8 ml of 10N sodium hydroxide. After being stirred for one hour, the suspension is filtered and the product is dried under partial vacuum at 50° C.

In this manner, 11.02 g of 10-(3-diethylamino-propylamino) 6-methyl 5H-pyrido[3',4':4,5]pyrrolo[2,3-g]isoquinoline are obtained in the form of a greenish powder.

Yield: 76%.

M.p.: 222° C.

| Elemental analysis %: (corresponding to the hemihydrate: ½ H$_2$O) | | | |
|---|---|---|---|
| | C | H | N |
| Calculated | 71.35 | 7.57 | 18.92 |
| Found | 71.23 | 7.47 | 19.02 |

| I.R. spectrum (KBr): | |
|---|---|
| NH | 3500–3000 cm$^{-1}$ (m, w) |
| aromatic C=N, C=C | 1635 cm$^{-1}$ (m) |
| | 1610 cm$^{-1}$ (S) |
| | 1575 cm$^{-1}$ (m) |

NMR spectrum (D$_4$-methanol): 1.0 ppm (t,6H); 1.6–2.1 ppm (m,2H); 2.2–2.8 ppm (m,9H); 3.2–3.7 ppm (m,2H); 4.9 ppm (m,2H); 6.85 ppm (d,1H); 7.25 ppm (d,1H); 7.65 ppm (d,1H); 8.25 ppm (d,1H); 8.40 ppm (s,1H); 9.0 ppm (s,1H).

EXAMPLE 39

Preparation of 10-(3-diethylamino-propylamino) 5H-pyrido[3',4':4,5]pyrrolo[2,3-g]isoquinoline 0.87 g (0.0033 mole) of 10-methoxy 6-methyl 5H-pyrido[3',4':4,5]pyrrolo[2,3-g]isoquinoline and 0.495 g (0.003 mole) of sodium iodide are suspended in 25 ml of acetonitrile and 4.2 ml (0.33 mole) of trimethylsilylchloride, and then heated at 40° C. for 17 hours. 10.5 ml (0.050 mole) of hexamethyldisilazane, 0.113 g (6×10$^{-4}$ mole) of anhydrous p-toluenesulfonic acid and 22.4 ml (0.14 mole) of diethylaminopropylamine are then added. After distillation of the acetonitrile, the mixture is heated at reflux for 20 hours. It is evaporated to dryness under a partial vacuum and the residue is stirred with 20 ml of water and 5 ml of diisopropyl ether for 1 hour. The precipitate obtained is filtered off and dried under vacuum at 50° C.

Thus are obtained 1.040 g of a brown solid which is purified by chromatography on silica.

0.43 g of 10-(3-diethylamino-propylamino) 6-methyl 5H-pyrido[3',4':4,5]pyrrolo[2,3-g]isoquinoline are obtained in this way. Yield: 36%.

EXAMPLE 40

Preparation of 10-(3-diethylamino-propylamino) 6-methyl 5H-pyrido[3',4':4,5]pyrrolo[2,3-g]isoquinoline (a) 10-chloro 6-methyl 5H-pyrido[3',4':4,5]pyrrolo[2,3-g]isoquinoline 20 g (0.076 mole) of 10-methoxy 6-methyl 5H-pyrido[3',4':4,5]pyrrolo[2,3-g]isoquinoline, 48.6 ml (0.304 mole) of diethylaniline and 69.24 g (0.304 mole) of benzyl triethylammonium chloride are dissolved in 200 ml of dry acetonitrile. 349 ml (3.8 moles) of phosphorous trichloride are then added in the space of a few minutes and the suspension obtained is heated at reflux for 6 hours. The acetonitrile and the excess phosphorous trichloride are removed by distillation under reduced pressure.

The oily residue is gradually hydrolyzed by the addition of 930 ml of water and the pH of the medium is then brought to 8 by the addition of 10N sodium hydroxide. The precipitate is washed with 100 ml of water and the second precipitate formed in the filtrate is filtered off. The 2 precipitates are pooled and the solid obtained is stirred after having been suspended in 300 ml of acetone. After filtration and drying under reduced pressure at 50° C., 17 g of 10-chloro 6-methyl 5H-pyrido[3',4':4,5]pyrrolo[2,3-g]isoquinoline are obtained in the form of a yellowish brown solid.

Yield: 83%.
M.p.: >263° C.
Chlorine content, 13.25% (theory: 13.24%).

| I.R. spectrum (KBr): | |
|---|---|
| C=N, C=C aromatic C—C | 1615, 1600 cm$^{-1}$ |

NMR spectrum (trifluoroacetic acid): 3.15 ppm (s,3H); 8.0–9.7 ppm (m,6H).

(b) 10-(3-diethylamino-propylamino) 6-methyl 5H-pyrido[3',4':4,5]pyrrolo[2,3-g]isoquinoline 5.9 g (0.022 mole) of 10-chloro 6-methyl 5H-pyrido[3',4':4,5]pyrrolo[2,3-g]isoquinoline are suspended in 149 ml (0.946 mole) of diethylaminopropylamine and the suspension is heated at 150° C. for 5 hours. Excess amine is distilled under reduced pressure and a yellow solid is obtained which is taken up in 106 ml of water and 22 ml of 1N sodium hydroxide.

After being stirred for one hour, the suspension is filtered through a glass frit and the solid collected is washed with diisopropyl ether and dried in a partial vacuum at 50° C.

6.75 g of 10-(3-diethylamino-propylamino) 6-methyl 5H-pyrido[3',4':4,5]pyrrolo[2,3-g]isoquinoline are thus obtained in the form of a yellow solid.

Yield: 85%.
M.p.: 223° C.

EXAMPLE 41

Preparation of the trimaleate of 10-(3-diethylamino-propylamino) 6-methyl 5H-pyrido[3',4':4,5]pyrrolo[2,3-g]isoquinoline (A) 10-chloro 6-methyl 5H-pyrido[3',4':4,5]pyrrolo[2,3-g]isoquinoline 1.053 g (0.004 mole) of 10-methoxy 6-methyl 5H-pyrido[3',4':4,5]pyrrolo[2,3-g]isoquinoline are suspended in 5.6 ml (0.040 mole) of dichlorophenylphosphine oxide and the suspension is heated at 160° C. for 2 hours. The reaction mixture is poured onto ice and the pH is brought to 7 by the addition of 10N sodium hydroxide. After filtration and drying of the precipitate formed, 0.580 g of 10-chloro 6-methyl 5H-pyrido[3',4':4,5]pyrrolo[2,3-g]isoquinoline are obtained.

Yield: 54%.

(B) 10-(3-diethylamino-propylamino) 6-methyl 5H-pyrido[3',4':4,5]pyrrolo[2,3-g]isoquinoline This compound was obtained according to the method described in Example 40b.

(C) Trimaleate of 10-(3-diethylamino-propylamino) 6-methyl 5H-pyrido [3',4':4,5]pyrrolo[2,3-g]isoquinoline 5.06 g (0.014 mole) of 10-(3-diethylamino-propylamino) 6-methyl 5H-pyrido[3',4':4,5]pyrrolo[2,3-g]isoquinoline are dissolved in 47 ml of methanol and 4.87 g (0.042 mole) of maleic acid dissolved in 47 ml of methanol are added during 5 minutes. After the reaction mixture has been stirred for one hour at 20° C. the dense precipitate is filtered off onto a glass frit and rinsed with 5 ml of methanol. It is then dried under a partial vacuum at 50° C.

9.15 g of the trimaleate of 10-(3-diethylamino-propylamino) 6-methyl 5H-pyrido[3',4':4,5]pyrrolo[2,3-g]isoquinoline are thus obtained in the form of a pale yellow powder.

Yield: 92%.
M.p.: about 225° C. (not sharp).

| | Elemental analysis %: | | | |
|---|---|---|---|---|
| | C | H | N | O |
| Calculated | 57.53 | 5.55 | 9.87 | 27.05 |
| Found | 57.33 | 5.57 | 9.61 | 26.92 |

| I.R. spectrum (KBr): | |
|---|---|
| OH, NH$^+$, NH$_2^+$ | 3200–2300 cm$^{-1}$ (m, w) |
| C=O, C—C | 1625, 1585 cm$^{-1}$ (m) |
| COO$^-$ | 1470 cm$^{-1}$ (m, w) |

NMR spectrum (trifluoroacetic acid): 1.5 ppm (t,6H); 2.5 ppm (m,2H); 3.0 ppm (s,3H); 3.0–4.0 ppm (m,8H); 6.65 ppm (s,6H); 7.7–9.6 ppm (m,6H).

EXAMPLE 42

Preparation of 1-(3-diethylamino-propylamino) 5,11-dimethyl 6H-pyrido [4,4-b]carbazole (formula I:Am=3-diethylamino-propylamino, X=OCH$_3$, R$_1$=R'$_1$=CH$_3$)

0.245 g (8×10$^{-4}$ mole) of 1,9-dimethoxy 5,11-dimethyl 6H-pyrido [4,3-b]carbazole are placed in a mixture of 26 ml (0.0165 mole) of diethylaminopropylamine and 0.28 ml (0.0032 mole) of trifluoromethane sulfonic acid in methanol.

The mixture is heated gradually to the reflux temperature of the amine, during which time the methanol is distilled. The reaction mixture is then maintained between 150° and 160° C. for about 13 hours. Excess amine is distilled under reduced pressure, the residue is taken up in 5 ml of water and neutralized by the addition of 0.15 ml of 10N sodium hydroxide. After being stirred for 1 hour, the suspension is filtered and the product is dried under partial vacuum at 50° C.

0.112 g of 1-(3-diethylamino-propylamino) 5,11-dimethyl 6H-pyrido [4,3-b]carbazole are thus obtained after chromatography on silica.

Yield: 35%.

M.p.: 156° C.

NMR spectrum (DMSOD$_6$): 0.7–1.7 ppm (m,12H); 2.6 ppm (m,5H); 3.2 ppm (m,2H); 3.5 ppm (s,3H); 3.9 ppm (s,3H); 4.0–4.2 ppm (m,2H); 6.5–8 ppm (m,5H).

We claim:

1. A process for the preparation of isoquinoline derivatives of the formula:

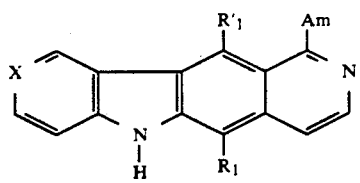

and their pharmaceutically acceptable salts, in which:
R$_1$ and R'$_1$, are identical or different, wherein each is either hydrogen or a C$_{1-4}$ alkyl,
X is either nitrogen or C—OR$_2$, wherein R$_2$ is either a C$_{1-4}$ alkyl or a benzyl,
Am represents an amino group that is unsubstituted or substituted by a group of the formula:

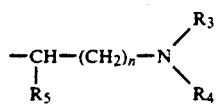

in which R$_3$ and R$_4$ are identical or different, wherein each is either hydrogen or an alkyl having from 1 to 6 carbon atoms, R$_5$ is either from hydrogen or an alkyl having 1 to 6 carbon atoms, and n represents a value of from 1 to 10, comprising the following steps:
step I:
(a) a compound of the formula

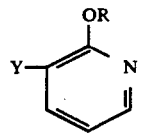

in which:
R is C$_{1-4}$ alkyl
Y is either 4,4-dimethyl-2-oxazolinyl or a group having the formula:

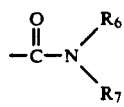

in which R$_6$ and R$_7$ are identical or different, are C$_{1-4}$ alkyl, is converted into a metalated derivative of the formula:

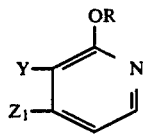

in which Z$_1$ is either lithium or a radical of the formula —Mg Hal, —Mn Hal or —Ce(Hal)$_2$, wherein Hal represents a halogen, wherein the metalated derivative of the formula IVa is then condensed with a heterocyclic compound of the formula:

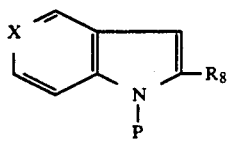

in which:
X has the same meaning as before,
P represents a labile protecting group, and
R$_8$ represents:
a radical of the formula

in which R$_1$ is selected from the group consisting of hydrogen, C$_{1-4}$ alkyl, and a radical of the formual

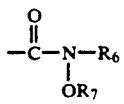

in which R$_6$ and R$_7$ are identical or different and, have the same meanings as before, or
(b) a compound of the formula:

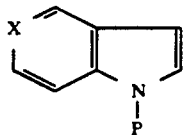

IIIb in which X and P have the same meanings as before, is converted into a metalated derivative of the formula:

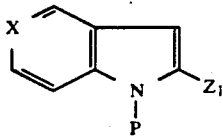

IVb in which X, P, and $Z_1$ have the same meanings as before, wherein the metalated derivative of formula IVb is condensed with a derivative of 2-alkoxypyridine of the formula:

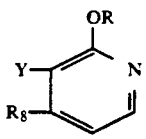

Vb in which Y, R, and $R_8$ have the same meanings as before so as to give rise to
in the case in which $R_8$ is a

radical, a compound of the formula:

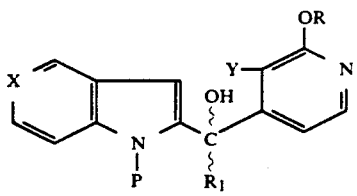

II in which X, P, Y, R, and $R_1$ have the same meanings as before, and
in the case in which $R_8$ is a radical of the formula

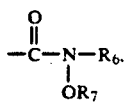

a compound of the formula:

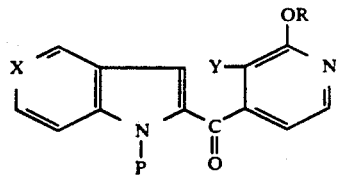

VI in which P, R, X, and Y have the same meanings as before, a compound which is subsequently treated by means of a reducing agent selected from an alkali metal borohydride, lithium aluminium hydride and an alkylmetal of the formula:

$R_9M$      VII in which $R_9$ represents $C_{1-4}$ alkyl and M is either lithium or —MgHal in which Hal represents halogen in order to give rise to a complex which is hydrolyzed to give a compound of the formula II and, if necessary, the compound of the formula II, in which $R_1$ represents hydrogen is oxidized to a compound of the formula VI which is subsequently treated with an alkylmetal of the formula VII and then hydrolyzed to give rise to a compound of the formula II in which $R_1$ represents $C_{1-4}$ alkyl, the compound of the formula II obtained in this first step being subsequently deprotected by treatment with a basic agent so as to give rise to a N-deprotected compound, if desired;

step II:
the compound of the formula II or the N-deprotected compound is treated with a pharmaceutically acceptable acid to form a lactone of the formula:

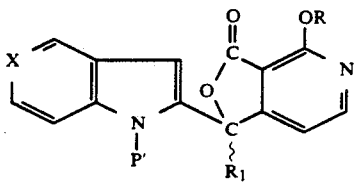

VIII in which X, R, $R_1$ have the same meanings as before and P' designates a labile protecting group P or hydrogen, and the lactone thus obtained is reduced either by means of a metal hydride in order to give rise to a cyclic hemiacetal of the formula:

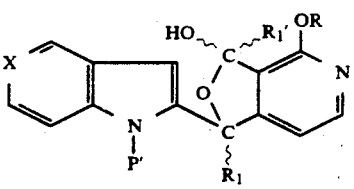

IX in which P', R, $R_1$, and X have the same meanings as before, and $R'_1$ represents hydrogen or by means of an alkyl magnesium halide of the formula VII, with hydrolysis of the complex formed, to give rise to a hemiacetal of the formula IX in which $R'_1$ is an alkyl radical of $C_{1-4}$ and, if desired, a deprotection is carried out;

step III:

a compound of the formula IX is converted into a compound of the formula:

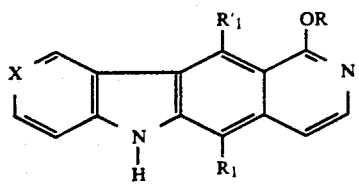     X in which R, $R_1$, or $R_1'$ and X have the same meanings as before; either directly by treating the compound of formula IX with from 10 to 15 molar equivalents of an alkali metal hydroxide in a lower alcohol under reflux; or indirectly by treating the compound of formula IX with from 1 to 15 molar equivalents of an alkali metal hydroxide in a $C_1$–$C_3$ alcohol at a temperature varying between $-5°$ C. and $50°$ C. and further treating the compound so obtained by means of an alkali metal borohydride to give rise to the desired compound of formula X;

step IV:

a compound of the formula X is treated with either (a) a compound of the formula:

H—Am     XI in which Am has the same meaning as before, in the presence of an acid catalyst in order to give rise to the desired compound of the formula I in the form of the free base, or (b) dichlorophenylphosphine oxide in order to give rise to a chloro compound of the formula:

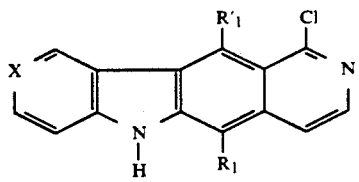     XII in which $R_1$, $R'_1$ and X have the same meanings as before, which is made to react with a compound of the formula XI in order to form the desired compound of the formula I in the form of the free base, or (c) phosphorous trichloride in the presence of a mixture of a nitrile-cosolvent, an ammonium chloride and an aniline in order to form a chloro compound of the formula XII which is made to react with a compound of the formula XI in order to give rise to the desired compound of the formula I in the form of the free base, or (d) a trimethylsilyl halide in the presence of an alkali metal halide in order to give rise to a trimethylsilyloxy derivative which is made to react with a compound of the formula XI in the presence of hexamethyldisilazane and p-toluenesulfonic acid in order to form the desired compound of the formula I in the form of the free base, a free base which, if necessary, can be treated with a suitable inorganic or organic acid in order to give rise to a pharmaceutically acceptable salt.

2. A process for the preparation of derivatives of alkoxyisoquinoline of the formula:

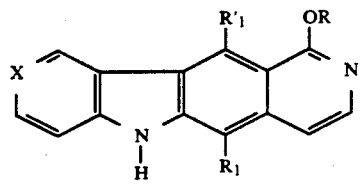     X in which:

$R_1$ and $R_1'$ are identical or different, and wherein each is either hydrogen or $C_{1-4}$ alkyl, R is $C_{1-4}$ alkyl, X is selected from nitrogen and C—$OR_2$ group in which $R_2$ is either $C_{1-4}$ alkyl or a benzyl, comprising the following steps:

step I:

(a) a compound of formula:

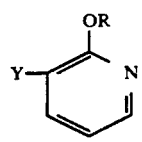     IIIa in which:

R has the same meaning as before and

Y is either 4,4-dimethyl 2-oxazolinyl or a group of the formula:

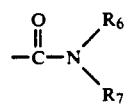

in which $R_6$ and $R_7$ are identical or different, and each is a $C_{1-4}$ alkyl, wherein the compound of the formula IIIa is converted into a metalated derivative of the formula:

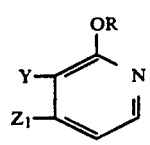     IVa in which $Z_1$ is either lithium or a radical of the formula —Mg Hal, —Mn Hal or —Ce(Hal)$_2$, wherein Hal is a halogen, and wherein the metalated derivative of the formula IVa is condensed with a heterocyclic compound of the formula:

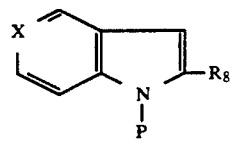     Va in which

X has the same meaning as before,

P represents a labile protecting group,

R₈ represents:

a radical of the formula

in which R₁ has the same meaning as before, or a radical of the formula

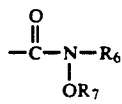

in which R₆ and R₇ are identical or different, having the same meanings as before, or, (b) a compound of the formula:

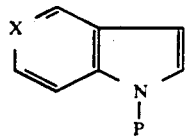

IIIb in which X and P have the same meanings as before, is converted into a metalated derivative of the formula:

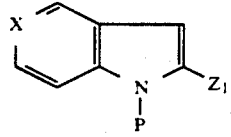

IVb in which X, P, and Z₁ have the same meanings as before, wherein the metalated derivative of the formula IVb is then condensed with a derivative of 2-alkoxy pyridine of the formula;

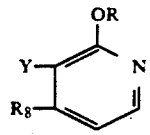

Vb in which Y, R, and R₈ have the same meanings as before so as to give rise to in the case in which R₈ is a

radical, a compound of the formula:

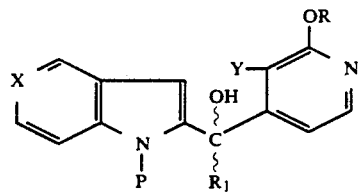

II in which X, P, Y, R, and R₁ have the same meanings as before, and in the case in which R₈ is a radical of formula

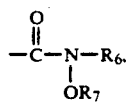

a compound of the formula:

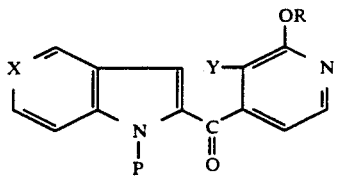

VI in which P, R, X, and Y have the same meanings as before, a compound which is subsequently treated by means of a reducing agent selected from the group consisting of an alkali metal borohydride, lithium aluminium hydride, and an alkylmetal of the formula:

R₉M    VII in which R₉ represents C₁₋₄ alkyl and M is either lithium or an —Mg Hal radical in which Hal represents halogen in order to give rise to a complex which is hydrolyzed to give a compound of the formula II and, if required, the compound of the formula II in which R₁ represents hydrogen is oxidized to the compound of the formula V which is subsequently treated with an alkylmetal of the formula VII and then hydrolyzed in order to give rise to a compound of the formula II in which R₁ represents C₁₋₄ alkyl, the compound of the formula II obtained in this first step being subsequently deprotected by treatment with a basic reagent so as to give rise to a N-deprotected compound, if desired;

step II:

the compound of the formula II or the N-deprotected compound is treated with a pharmaceutically acceptable acid to form a lactone of the formula:

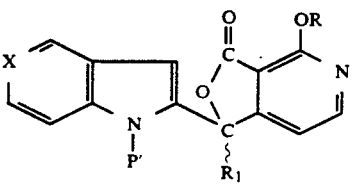

VIII in which X, R, and R₁ have the same meanings as before and P' designates a labile protecting group P or hydrogen wherein the lactone thus obtained is reduced either by means of a metal hydride in order to give rise to a cyclic hemiacetal of formula:

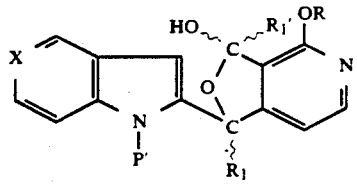

IX in which P', R, R₁, and X have the same meanings as before, and R'₁ represents a hydrogen atom, or by means of an alkylmagnesium halide of the formula VII, with hydrolysis of the complex formed, to give rise to a hemiacetal of the formula IX in which R'₁ is $C_{1-4}$ alkyl and, if desired, a deprotection is carried out;

step III:
a compound of the formula IX is converted into a compound of the formula X either
directly by treating the compound of formula IX with from 10 to 15 molar equivalents of an alkali metal hydroxide in a lower alcohol under reflux; or
indirectly by treating the compound of formula IX with from 1 to 15 molar equivalents of an alkali metal hydroxide in a $C_1$–$C_3$ alcohol at a temperature varying between −5° C. and 50° C. and further treating the compound so obtained by means of an alkali metal borohydride to give rise to the desired compound of formula X.

3. A process according to claim 1, wherein the stabilization reagent is selected from tetramethylethylenediamine and a tris(dioxaalkyl)amine.

4. A process according to claim 1, wherein the branched alkyllithium is tertiary butyllithium and the lithium amide is selected from the group consisting of lithium diethylamide, lithium diisopropylamide, and lithium 2,2,6,6-tetra-methylpiperidide.

5. A process according to claim 1, wherein, in the second step, the metal hydride is diisobutylaluminium hydride.

6. A process according to claim 1, wherein, in the second step, the deprotection is carried out:
(a) by treating a cyclic hemiacetal of formula IX in which P' represents a labile group, with boron trifluoride etherate in an alcohol of the formula:

$R_{13}OH$  XXIV in which R₁₃ represents $C_{1-4}$ alkyl in order to give rise to a ketal of the general formula:

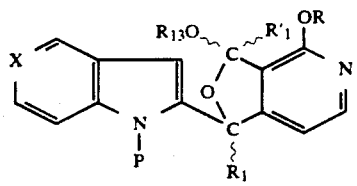

XXV in which P, R, R₁, R'₁, R₁₃ and X have the same meanings as in claim 1,
(b) by making the ketal of formula XXV react in a solvent with a basic reagent in order to give rise to a deprotected compound of the general formula:

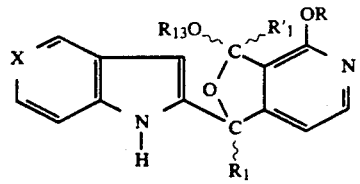

XXVI in which R, R₁, R'₁, R₁₃ and X have the same meanings as before,
(c) by hydrolyzing the protected compound of formula XXV in the presence of an acidic reagent in order to give rise to a cyclic hemiacetal of formula IX in which P' is hydrogen.

7. A process according to claim 1, wherein, in the third step, the conversion is carried out by treating the hemiacetal of formula IX with from 10 to 15 equivalents of an alkali metal hydroxide in a lower alcohol under reflux.

8. A process according to claim 1, wherein, an equivalent of hemiacetal of formula IX, in which X represents a nitrogen atom, P' represents a labile group and R'₁ represents a hydrogen atom, is treated with 10 to 15 equivalents of an alkali metal hydroxide for 15 to 20 hours in methanol at reflux or 1 to 2 hours in ethanol at reflux in order to form the alkoxy-isoquinoline derivatives of formula X, in which X represents a nitrogen atom, R represents an alkyl radical of $C_1$–$C_4$ and R' represents a hydrogen atom.

9. A process according to claim 1, wherein an equivalent of hemiacetal of formula IX, in which X represents a C—OR₂ group and R'₁ represents an alkyl radical of $C_1$–$C_4$, is treated with 10 to 15 equivalents of an alkali metal hydroxide for 12 to 15 hours in methanol at reflux in order to form the alkoxy-isoquinoline derivatives of formula X, in which X represents a C—OR₂ group and R and R'₁ each represents $C_{1-4}$ alkyl.

10. A process according to claim 1, wherein an a molar equivalent of hemiacetal of the formula IX, in which X represents a C—OR₂ group, P' represents a labile group and R'₁ represents hydrogen, is treated with 10 to 15 molar equivalents of an alkali metal hydride for 1 to 2 hours in methanol at reflux in order to form the alkoxy-isoquinoline derivatives of the formula X, in which X represents a C—OR₂ group, R'₁ represents a hydrogen atom.

11. A process according to claim 1, wherein, in the third step, the conversion is carried out by making a compound of formula IX, in which X represents nitrogen react with an alkali metal hydroxide in a $C_{1-3}$ alcohol at a temperature varying from −5° C. to ambient temperature in order to form an isoquinoline derivative of the formula:

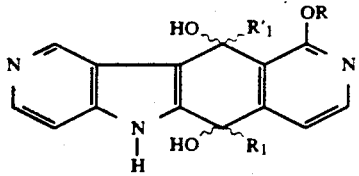

XXVII in which R, $R_1$ and $R'_1$ have the same meanings as in claim 1, isoquinoline derivatives which are treated with an alkali metal borohydride in order to form a compound of formula X, in which X represents nitrogen.

12. A process according to claim 11, wherein a molar equivalent of a phthalide derivative of formula IX, in which X represents a nitrogen atom and P' represents hydrogen is made to react with an equivalent of sodium hydroxide, the reaction being allowed to take place for 3 to 4 hours.

13. A process according to claim 11, wherein a molar equivalent of a phthalide derivative of formula IX, in which X represents a nitrogen, P' represents a labile group and $R_1$ represents $C_{1-4}$ alkyl, is made to react with 4 to 5 equivalents of sodium hydroxide during 2 to 8 hours.

14. A process according to claim 1, wherein, in the third step, the conversion is carried out by making a phthalide derivative of formula IX, in which X represents a $C-OR_2$ group and $R'_1$ represents $C_{1-4}$ alkyl react with an alkali metal hydroxide in a $C_{1-3}$ alcohol at a temperature varying from 40° to 50° C. in order to form an alkenyl derivative of the formula:

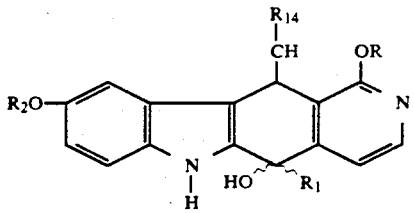

XXVIII in which R, $R_1$ and $R_2$ have the same meanings as in claim 1 and $R_{14}$ is selected from hydrogen and $C_{1-4}$ alkyl, an alkenyl derivative which is treated with an alkali metal borohydride in order to form the desired derivative of formula X, in which X represents a $C-OR_2$ group.

15. A process according to claim 14, wherein an equivalent of a phthalide derivative of formula IX, in which X represents a $C-OR_2$ group, $R'_1$ represents $C_{1-4}$ alkyl and P' represents hydrogen, is made to react with 10 to 15 equivalents of potassium hydroxide during 3 to 4 hours.

16. A process according to claim 11, wherein the treatment with the alkali metal borohydride is carried out in a glycol ether as solvent at a temperature varying between 100° C. and the reflux temperature.

17. A process according to claim 1, wherein in Step I, a compound of the formula IIIa is converted into a metalated derivative of the formula IVa in which $Z_1$ represents lithium.

18. A process according to claim 1 wherein in Step I, a compound of formula IIIb is converted into a metalated derivative of the formula IVb in which $Z_1$ represents lithium with a lithiation reagent which is either a branched alkyl lithium or a lithium amide, at a temperature varying between −80° C. and −20° C. in the presence of a stabilization reagent, and wherein the then metalated derivative obtained is condensed at a temperature varying between −80° C. and −20° C.

19. A process according to claim 1, wherein, in Step I, a compound of the formula IIIa is converted into a metalated derivative of the formula IVa in which $Z_1$ is a radical of the formula —Mg Hal, —Mn Hal or —Ce(Hal)$_2$.

20. A process according to claim 1 wherein, in Step I, a compound of the formula IIIb is converted into a metalated derivative of the formula IVb in which $Z_1$ represents a radical of the formula —Mg Hal, —Mn Hal or —Ce(Hal)$_2$ by transmetalation of a lithiated derivative of the formula:

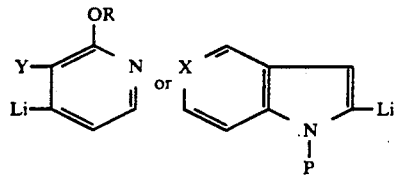

in which R, X, Y, and P have the same meanings as before.

21. A process according to claim 2, wherein, in Step I, a compound of formula IIIa is converted into a metalated derivative of formula IVa in which $Z_1$ is a radical of the formula —Mg Hal, —Mn Hal or —Ce(Hal)$_2$.

22. A process according to claim 2, wherein, in Step I, a compound of the formula IIIb is converted into a metalated derivative of the formula IVb in which $Z_1$ represents a radical of the formula —Mg Hal, —Mn Hal, or —Ce(Hal)$_2$ by transmetalation of a lithiated derivative of the formula:

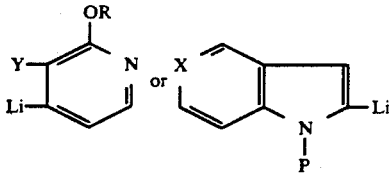

in which R, X, Y, and P have the same meanings as before.

* * * * *